United States Patent
Juhl et al.

(10) Patent No.: US 10,045,974 B2
(45) Date of Patent: Aug. 14, 2018

(54) 2-AMINO-6-(DIFLUOROMETHYL)-5,5-DIFLUORO-6-PHENYL-3,4,5,6-TETRAHYDROPYRIDINES AS BACE1 INHIBITORS

(71) Applicant: H. Lundbeck A/S, Valby (DK)

(72) Inventors: Karsten Juhl, Greve (DK); Lena Tagmose, Lyngby (DK); Mauro Marigo, Skovlunde (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/524,546

(22) PCT Filed: Nov. 9, 2015

(86) PCT No.: PCT/EP2015/076015
§ 371 (c)(1),
(2) Date: May 4, 2017

(87) PCT Pub. No.: WO2016/075063
PCT Pub. Date: May 19, 2016

(65) Prior Publication Data
US 2017/0319564 A1 Nov. 9, 2017

(30) Foreign Application Priority Data

Nov. 10, 2014 (DK) .................. 2014 00648
Aug. 7, 2015 (DK) .................. 2015 00447

(51) Int. Cl.
*C07D 401/12* (2006.01)
*A61K 31/4439* (2006.01)
*C07D 417/12* (2006.01)
*C07D 413/12* (2006.01)

(52) U.S. Cl.
CPC ........ *A61K 31/4439* (2013.01); *C07D 401/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 7,067,507 B2 | 6/2006 | Pulley et al. | |
| 8,338,413 B1 | 12/2012 | Rueeger | |
| 9,346,797 B1 | 5/2016 | Juhl et al. | |
| 9,353,084 B2 | 5/2016 | Juhl et al. | |
| 2011/0009395 A1 | 1/2011 | Audia et al. | |
| 2014/0371212 A1 | 12/2014 | Green et al. | |
| 2015/0232449 A1 | 8/2015 | Juhl et al. | |
| 2016/0130267 A1 | 5/2016 | Juhl et al. | |
| 2017/0042895 A1 | 2/2017 | Juhl et al. | |
| 2017/0044151 A1 | 2/2017 | Juhl et al. | |
| 2017/0066741 A1 | 3/2017 | Juhl et al. | |
| 2017/0313658 A1 | 11/2017 | Juhl et al. | |
| 2017/0340618 A1 | 11/2017 | Juhl et al. | |

FOREIGN PATENT DOCUMENTS

| | | |
|---|---|---|
| EP | 2703399 | 3/2014 |
| WO | WO 2003/032970 | 4/2003 |
| WO | WO 2003/068747 | 8/2003 |
| WO | WO 2011/154431 | 12/2011 |
| WO | WO 2012/095463 | 7/2012 |
| WO | WO 2012/095469 | 7/2012 |
| WO | WO 2012/139993 | 10/2012 |
| WO | WO 2012/168164 | 12/2012 |
| WO | WO 2013/027188 | 2/2013 |
| WO | WO 2013/142613 | 9/2013 |
| WO | WO 2014/056816 | 4/2014 |
| WO | WO 2014/065434 | 5/2014 |
| WO | WO 2014/134341 | 9/2014 |
| WO | WO 2015/124576 | 8/2015 |
| WO | WO 2015/156421 | 10/2015 |
| WO | WO 2016/075062 | 5/2016 |
| WO | WO 2016/075063 | 5/2016 |
| WO | WO 2016/075064 | 5/2016 |
| WO | WO 2017/025559 A1 | 2/2017 |

OTHER PUBLICATIONS

Hilpert, H. et al. (2013) "β-Secretase (BACE1) Inhibitors With High In Vivo Efficacy Suitable for Clinical Evaluation in Alzheimer's Disease," J. Med. Chem. 56(10):3980-3995.
Oehlrich, D. et al. (2014) "The Evolution of Amidine-Based Brain Penetrant BACE1 Inhibitors," Bioorg. Med. Chem. Lett. 24(9):2033-2045.
International Search Report PCT/EP2015/076015 (WO 2016/075063) (2016) (5 pages).
Written Opinion of the International Searching Authority PCT/EP2015/076015 (WO 2016/075063) (2016) (4 pages).
International Search Report and Written Opinion dated Oct. 18, 2016 in connection with PCT/EP2016/068947.
International Search Report and Written Opinion dated Sep. 12, 2016 in connection with PCT/EP2016/069029.
International Search Report and Written Opinion dated Mar. 8, 2018 in connection with PCT/EP2017/083484.
Anonymous (2014) "Understanding Genetics and Alzheimer's Disease," Alzheimer Society, pp. 1-4.
Asuni, A., et al. (2007) "Immunotherapy Targeting Pathological Tau Conformers in a Tangle Mouse Model Reduces Brain Pathology with Associated Functional Improvements," J. Neurosci. 27:9115-9129.

(Continued)

*Primary Examiner* — Zinna Northington Davis
(74) *Attorney, Agent, or Firm* — Wolf, Greenfield & Sacks, P.C.

(57) ABSTRACT

The present invention is directed to compounds of formula (I) which are inhibitors of the BACE1 enzyme. Separate aspects of the invention are directed to pharmaceutical compositions comprising said compounds and uses of the compounds to treat disorders for which the reduction of Aβ deposits is beneficial such as Alzheimer's disease.

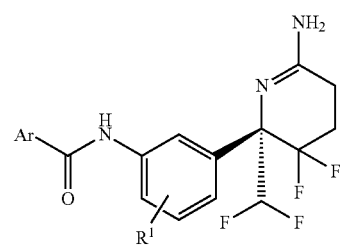

(I)

3 Claims, 1 Drawing Sheet

(56) References Cited

OTHER PUBLICATIONS

Bakker, A., et al. (2012) "Reduction of Hippocampal Hyperactivity Improves Cognition in Amnestic Mild Cognitive Impairment," Neuron 74(3):467-474.
Berge, S.M., et al. (1977) "Pharmaceutical Salts," J. Pharma. Sci. 66:1-19.
Bermejo-Bescós, P., et al. (2013) "Processing of the Platelet Amyloid Precursor Protein in the Mild Cognitive Impairment (MCI)," Neurochem. Res. 38:1415-1423.
Biffi, A. et al. (2011) "Cerebral Amyloid Angiopathy: A Systematic Review," J. Clin. Neurol. 7:1-9.
Bohm, C. et al. (2015) "Current and Future Implications of Basic and Translational Research on Amyloid-β Peptide Production and Removal Pathways," Mol. Cell. Neurosci. 66:3-11.
Boutajangout, A. et al. (2010) "Immunotherapy Targeting Pathological Tau Prevents Cognitive Decline in a New Tangle Mouse Model," J. Neurosci. 30(49):16559-16566.
Boutajangout, A., et al. (2011) "Targeting Hyperphosphorylated Tau Protein with a Monoclonal Antibody at an Advanced Stage of Tau Pathology Improves Cognition in a Mouse Model," 7(4,suppl):S480-S481.
Butchart, J., et al. (2015) "Etanercept in Alzheimer Disease: A Randomized, Placebo-Controlled, Double-Blind, Phase 2 Trial," Neurol. 84(21):2161-2168.
Cheng, X., et al. (2014) "High Activities of BACE1 in Brains with Mild Cognitive Impairment," Am. J. Pathol. 184:141-147.
Cheng, X., et al. (2014) "Occludin Deficiency with BACE1 Elevation in Cerebral Amyloid Angiopathy," Neurology 82:1707-1715.
Davtyan, H., et al. (2013) "Immunogenicity, Efficacy, Safety, and Mechanism of Action of Epitope Vaccine (Lu AF20513) for Alzheimer's Disease: Prelude to a Clinical Trial," J. Neurosci. 33(11):4923-4934.
DeMattos, R.B., et al. (2015) "Investigation of Dose-Responses and Longitudinal Effects of Combination Therapy with a Plaque-Specific Amyloid Beta Antibody and BACE Inhibitor in Aged Transgenic Mice," Alzheimer's & Dementia: J. Alzheimer's Assoc. 11(7 suppl):275-276.
Dubois, B. et al. (2007) "Research Criteria for the Diagnosis of Alzheimer's Disease: Revising the NINCDS-ADRDA Criteria," Lancet Neurol. 6:734-746.
Ginman, T., et al., (2013) "Core Refinement Toward Permeable β-Secretase (BACE1) Inhibitors with Low hERG Activity," J. Med. Chem. 56:4181-4205.
Hamada, Y., et al. (2009) "Recent Progress in the Drug Discovery on Non-Peptidic BACE1 Inhibitors," Expert Opinion on Drug Disc. 4(4):391-416.
Hampel, H., et al. (2009) "Beta-site Amyloid Precursor Protein Cleaving Enzyme 1 (BACE1) as a Biological Candidate Marker of Alzheimer's Disease," The Scandinavian J. Clin. Lab. Invest. 69(1):8-12.
Hartley, D., et al. (2015) "Down Syndrome and Alzheimer's Disease: Common Pathways, Common Goals," Alzheimer's & Dementia 11:700-709.
Heneka, M.T., et al. (2015) "Neuroinflammation in Alzheimer's Disease," Lancet Neurol. 14(4):388-405.
Hilpert, H., et al. (2013) "S1 Supporting Information β-Secretase (BACE1) Inhibitors with High In Vivo Efficacy Suitable for Clinical Evaluation in Alzheimer's Disease," 56:S1-S44.
Holler, C.J., et al. (2012) "BACE2 Expression Increases in Human Neurodegenerative Disease," Am. J. Pathol. 180:337-350.
International Search Report PCT/EP2015/053327 (WO 2015/124576) (dated 2015) (5 pages).
International Search Report PCT/EP2015/076014 (WO 2016/075062) (dated 2016) (4 pages).
International Search Report PCT/EP2015/076017 (WO 2016/075064) (dated 2016) (5 pages).
Jacobsen, H., et al. (2014) "Combined Treatment with a BACE Inhibitor and Anti-Aβ Antibody Gantenerumab Enhances Amyloid Reduction in APP$_{London}$ Mice," J. Neurosci. 34(35):11621-11630.
Jeon, S.Y., et al. (2003) "Green Tea Catechins as a BACE1 (β-Secretase) Inhibitor," Bioorganic & Medicinal Chem. Lett. 13:3905-3908.
Jeppsson, F., et al. (2012) "Discovery of AZD3839, a Potent and Selective BACE1 Inhibitor Clinical Candidate for the Treatment of Alzheimer Disease," J. Biol. Chem. 287(49):41245-41257.
Jiang, H., et al. (2011) "Elevated CSF Levels of TACE Activity and Soluble TNF Receptors in Subjects with Mild Cognitive Impairment and Patients with Alzheimer's Disease," Molecular Neurodegeneration 6:69.
Jiang, Y., et al. (2010) "Alzheimer's-Related Endosome Dysfunction in Down Syndrome in Aβ-independent but Requires APP and is Reversed by BACE-1 Inhibition," PNAS U.S.A. 107(4):1630-1635.
Jiang, Y., et al. (2016) "Partial BACE1 Reduction in a Down Syndrome Mouse Model Blocks Alzheimer-Related Endosomal Anomalies and Cholinergic Neurodegeneration: Role of APP-CTF," Neurobiol. Aging 39:90-98.
Koh, M.T., et al. (2010) "Treatment Strategies Targeting Excess Hippocampal Activity Benefit Aged Rates with Cognitive Impairment," Neuropsychopharmacol. 35:1016-1025.
Kumar, A., et al. (2015) "A Review on Alzheimer's Disease Pathophysiology and Its Management: An Update," Pharmacol. Reporting 67:195-203.
Malamas, M., et al. (2010) "Novel Pyrrolyl 2-Aminopyridines as Potent and Selective Human β-Secretase (BACE1) Inhibitors," Bioorganic & Medicinal Chem. Lett. 20:2068-2073.
Melis, V., et al. (2015) "Effects of Oxidized and Reduced Forms of Methylthioninium in Two Transgenic Mouse Tauopathy Models," Behav. Pharmacol. 26:353-368.
Miners, J.S., et al. (2011) "Accumulation of Insoluble Amyloid-β in Down's Syndrome is Associated with Increase BACE-1 and Neprilysin Activities," J. Alzheimer's Dis. 23:101-108.
Motonaga, K., et al. (2002) "Elevated Expression of Beta-Site Amyloid Precursor Protein Cleaving Enzyme 2 in Brains of Patients with Down Syndrome," Neurosci. Lett. 326:64-66.
Munro, K.M. et al. (2014) "BACE Inhibitor Arsenal Aimed at Early Stages of Alzheimer's Disease," JSM Alzheimer's Dis. Related Dementia 1(1):1005.
Ohno, M., et al. (2004) "BACE1 Deficiency Rescues Memory Deficits and Cholinergic Dysfunction in a Mouse Model of Alzheimer's Disease," Neuron 41:27-33.
Ohno, M., et al. (2007) "BACE1 Gene Deletion Prevents Neuron Loss and Memory Deificits in 5XFAD APP/PS1 Transgenic Mice," Neurobiology of Disease 26:134-145.
Probst, G., et al. (2012): Small-Molecule BACE1 Inhibitors: A Patent Literature Review (2006-2011), Expert Opinion on Thera. Patents 22(5):511-540.
Salminen, A., et al. (2017) "Hypoxia/ischemia Activate Processing of Amyloid Precursor Protein: Impact of Vascular Dysfunction in the Pathogenesis of Alzheimer's Disease," J. Neurochem. 140:536-549.
Scott, J.D. et al. (2016) "Discovery of the 3-Imino-1,2,4-thiadiazinane 1,1-Dioxide Derivative Verubecestat (MK-8931)—A β-Site Amyloid Precursor Protein Cleaving Enzyme 1 Inhibitor for the Treatment of Alzheimer's Disease," J. Med. Chem. 59:10435-10450
Sheline, Y.I., et al. (2014) "An Antidepressant Decreases CSF AβProduction in Healthy Individuals and in Transgenic AD Mice," Sci. Transl. Med. 6(236):236re4; pp. 1-10.
Shi, J.Q., et al. (2013) "Antiepileptics Topiramate and Levetiracetam Alleviate Behavioral Deficits and Reduce Neuropathology in APPswe/PS1dE9 Transgenic Mice," CNS Neurosci. Ther. 19(11):871-881.
Sun, X., et al. (2006) "Increased BACE1 Maturation Contributes to the Pathogenesis of Alzheimer's Disease in Down Syndrome," FASEB J. 20(9):1361-1368.
Thakker, D.R., et al. (2015) "Centrally Delivered BACE1 Inhibitor Activates Microglia, and Reverses Amyloid Pathology and Cognitive Deficit in Aged Tg2576 Mice," J. Neurosci. 35(17):6931-6936.
Vassar, R. (2014) "BACE1 Inhibitor Drugs in Clinical Trials for Alzheimer's Disease," Alzheimer's Research & Therapy 6(9):89.

(56) References Cited

OTHER PUBLICATIONS

Vossel, K.A., et al. (2013) "Seizures and Epileptiform Activity in the Early Stages of Alzheimer Disease," JAMA Neurol. 70(9):1158-1166.

Wang, J., et al. (2015) "Anti-inflammatory Drugs and Risk of Alzheimer's Disease: An Updated Systematic Review and Meta-Analysis," J. Alzheimers Dis. 44(2):385-396.

Wang, T., et al. (2016) "Abnormal Changes of Brain Cortical Anatomy and the Association with Plasma MicroRNA107 Level in Amnestic Mild Cognitive Impairment," Front. Aging Neurosci. 8:112.

Webb, R.L. et al. (2012) "β-Secretases, Alzheimer's Disease, and Down Syndrome," Current Gerontology and Geriatrics Research, vol. 2012, Article ID 362839, 8 pages.

Willem, M., et al. (2004) "β-Site Amyloid Precursor Protein Cleaving Enzyme 1 Increases Amyloid Deposition in Brain Parenchyma but Reduces Cerebrovascular Amyloid Angiopathy in Aging BACE x APP[V717I] Double-Transgenic Mice," Am. J. Pathol. 165(5):1621-1631.

Willem, M., et al. (2009) "Function, Regulation and Therapeutic Properties of β-Secretase (BACE1)," Seminars in Cell & Developmental Biol. 20:175-182.

Woltering, T.J., et al. (2013) "BACE1 Inhibitors: A Head Group Scan on a Series of Amides," Bioorganic & Medicinal Chem. Lett. 23:4239-4243.

Written Opinion of the International Searching Authority PCT/EP2015/053327 (WO 2015/124576) (dated 2015) (6 pages).

Written Opinion of the International Searching Authority PCT/EP2015/076014 (WO 2016/075062) (dated 2016) (5 pages).

Written Opinion of the International Searching Authority PCT/EP2015/076017 (WO 2016/075064) (dated 2016) (4 pages).

Xue, Z.Q., et al. (2015) "Non-Neuronal and Neuronal BACE1 Elevation in Association with Angiopathic and Leptomeningeal β-Amyloid Deposition in the Human Brain," BMC Neurology 15:71.

Zaitsev, A.V., et al. (2015) "N-methyl-D-aspartate Receptor Channel Blockers Prevent Pentylenetetrazole-Induced Convulsions and Morphological Changes in Rat Brain Neurons," J. Neurosci. Res. 93(3):454-465.

Zetterberg, H., et al. (2008) "Elevated Cerebrospinal Fluid BACE1 Activity in Incipient Alzheimer Disease," Arch. Neurol. 65(8):1102-1107.

Zhang, X., et al. (2015) "Upregulation of SET Expression by BACE1 and Its Implications in Down Syndrome," Mol. Neurobiol. 51:781-790.

Zhong, Z. et al. (2007) "Levels of β-Secretase (BACE1) in Cerebrospinal Fluid as a Predictor of Risk in Mild Cognitive Impairment," Arch. Gen. Psychiatry 64:718-726.

U.S. Appl. No. 15/751,765, filed Feb. 9, 2018, Pending.

U.S. Appl. No. 14/933,301, filed Nov. 5, 2015, Granted, U.S. Pat. No. 9,346,797.

U.S. Appl. No. 15/848,013, filed Dec. 20, 2017, Pending.

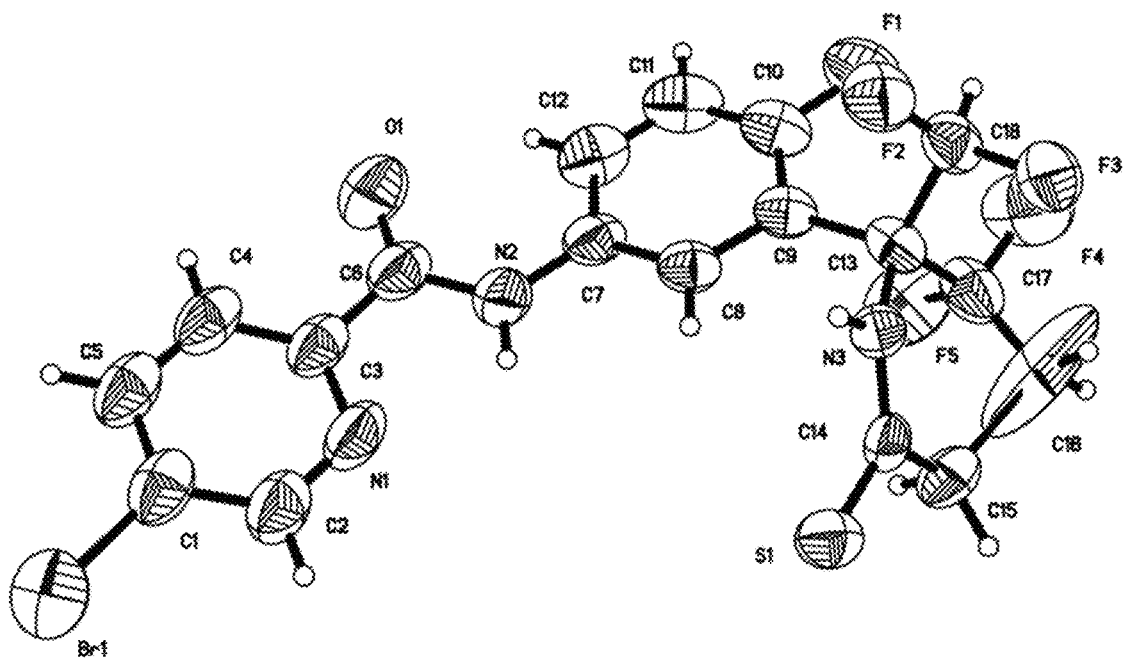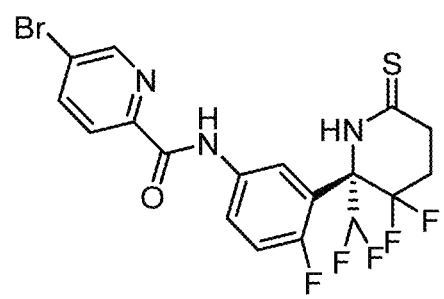

2-AMINO-6-(DIFLUOROMETHYL)-5,5-DIFLUORO-6-PHENYL-3,4,5,6-TETRAHYDROPYRIDINES AS BACE1 INHIBITORS

CROSS-REFERENCE TO RELATED APPLICATIONS

This application is a § 371 National Stage Application of PCT/EP2015/076015 (filed on Nov. 9, 2015), which application claims benefit of DK Patent Application No. PA 2015 00447, filed on Aug. 7, 2015, and DK Patent Application No. PA 2014 00648, filed on Nov. 10, 2014, each of which applications is hereby incorporated by reference in its entirety.

FIELD OF THE INVENTION

The present invention provides compounds which act as BACE1 inhibitors. Separate aspects of the invention are directed to pharmaceutical compositions comprising said compounds and uses of the compounds to treat neurodegenerative or cognitive disorders.

BACKGROUND ART

Dementia is a clinical syndrome characterized by deficits in multiple areas of cognition that cannot be explained by normal aging, a noticeable decline in function, and an absence of delirium. In addition, neuropsychiatric symptoms and focal neurological findings are usually present. Dementia is further classified based on etiology. Alzheimer's disease (AD) is the most common cause of dementia, followed by mixed AD and vascular dementia, Lewy body dementia (DLB), and fronto-temporal dementia. β-Amyloid deposits and neurofibrillary tangles are considered to be major pathologic characterizations associated with AD which is characterized by the loss of memory, cognition, reasoning, judgment, and orientation. Also affected, as the disease progresses, are motor, sensory and linguistic abilities until global impairment of multiple cognitive functions occurs. β-Amyloid deposits are predominantly an aggregate of Aβ peptide, which in turn is a product of the proteolysis of amyloid precursor protein (APP) as part of the β-amyloidogenic pathway. Aβ peptide results from the cleavage of APP at the C-terminal by one or more γ-secretases and at the N-terminal by β-secretase 1 (BACE1) also known as aspartyl protease 2. BACE1 activity is correlated directly to the generation of Aβ peptide from APP.

Studies indicate that the inhibition of BACE1 impedes the production of Aβ peptide. Further, BACE1 co-localizes with its substrate APP in Golgi and endocytic compartments (Willem M, et al. Semin. Cell Dev. Biol, 2009, 20, 175-182). Knock-out studies in mice have demonstrated the absence of amyloid peptide formation while the animals are healthy and fertile (Ohno M, et al. Neurobiol. Dis., 2007, 26, 134-145). Genetic ablation of BACE1 in APP-overexpressing mice has demonstrated absence of plaque formation, and the reverse of cognitive deficits (Ohno M, et al. Neuron; 2004, 41, 27-33). BACE1 levels are elevated in the brains of sporadic AD patients (Hampel and Shen, Scand. J. Clin. Lab. Invest. 2009, 69, 8-12).

These convergent findings indicate that the inhibition of BACE1 may be a therapeutic target for the treatment of AD as well as disorders for which the reduction of Aβ deposits is beneficial.

AstraZeneca announced the discovery of AZD3839, a potent BACE1 inhibitor clinical candidate for the treatment of AD (Jeppsson, F., et al. J. Biol. Chem., 2012, 287, 41245-41257) in October 2012. The effort which led to the discovery of AZD3839 was further described in Ginman, T., et al. J. Med. Chem., 2013, 56, 4181-4205. The Ginman publication describes the issues which were overcome in connection with the discovery and identification of AZD3839. These issues related to poor blood brain barrier penetration and P-glycoprotein mediated efflux of the compounds resulting in lack of brain exposure.

The Ginman manuscript hypothesized that the differences in brain exposure would largely be due to the core structures and Structure Activity Relationship data was provided wherein the in vitro properties on the reported compounds were given into four tables according to core sub-types. In table 4, a series of amidine containing compounds are described that were considered interesting from an activity perspective. However, the data suggests that the amidine containing core did not exhibit a favourable blood brain barrier permeability profile.

Researchers from Hoffmann-La Roche and Siena Biotech also reported the discovery of amidine containing compounds (Woltering, T. J., et al. Bioorg. Med. Chem. Lett. 2013, 23, 4239-4243). These compounds (compounds 17 and 18 in the paper) were found not to have any in vivo effect (lack of Aβ40 reduction in brain in wild type mice).

Contrary to the teachings of Ginman, et al. and Woltering, T. J., et al., the inventors have discovered a series of amidine compounds which are brain penetrant. Accordingly, the present invention relates to novel compounds having BACE1 inhibitory activity, to their preparation, to their medical use and to medicaments comprising them.

SUMMARY OF THE INVENTION

An objective of the present invention is to provide compounds that inhibit BACE1. Accordingly, the present invention relates to compounds of Formula I.

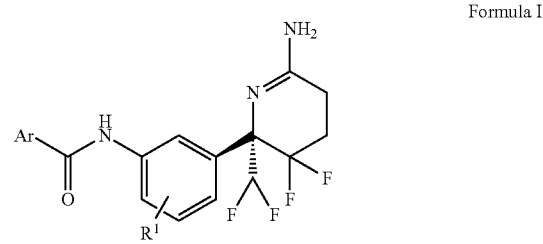

Formula I wherein Ar is selected from the group consisting of phenyl, pyridyl, pyrimidyl, pyrazinyl, imidazolyl, pyrazolyl, thiazolyl, oxazolyl, isoxazolyl, and where the Ar is optionally substituted with one or more substituent selected from halogen, CN, $C_1$-$C_6$ alkyl, $C_2$-$C_6$ alkenyl, $C_2$-$C_6$ alkenyl, $C_1$-$C_6$ fluoroalkyl or $C_1$-$C_6$ alkoxy; and R1 is hydrogen, halogen, $C_1$-$C_3$ fluoroalkyl or $C_1$-$C_3$ alkyl; or a pharmaceutically acceptable salt thereof.

In one embodiment the present invention provides compounds of Formula I or a pharmaceutically acceptable salt thereof for use in therapy.

The present invention further provides a pharmaceutical composition comprising a compound of Formula I or a pharmaceutically acceptable salt thereof and a pharmaceutically acceptable carrier.

In one embodiment the invention provides the use of a compound of Formula I or a pharmaceutically acceptable salt thereof in the manufacture of a medicament for the treatment of neurodegenerative or cognitive disorder.

In one embodiment, the invention provides a compound of Formula I or a pharmaceutically acceptable salt thereof for use in a method for the treatment of a neurodegenerative or cognitive disorder.

In one embodiment the present invention provides a method of treating a neurodegenerative or cognitive disorder comprising administering a therapeutically effective amount of a compound of Formula I or a pharmaceutically acceptable salt thereof to a patient in need thereof.

Further embodiments of the invention are provided immediately below:

In one embodiment, the compound is of formula Ia

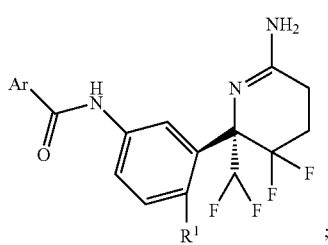

Formula Ia or a pharmaceutically acceptable salt thereof.

In one embodiment, $R^1$ is F or H, particularly F.

In one embodiment, Ar is optionally substituted with one or more F, Cl, Br, CN, $C_1$-$C_3$ alkyl, $C_1$-$C_3$ fluoroalkyl or $C_1$-$C_3$ alkoxy.

In one embodiment, Ar is optionally substituted phenyl.
In one embodiment, Ar is optionally substituted pyridyl.
In one embodiment, Ar is optionally substituted pyrimidyl.
In one embodiment, Ar is optionally substituted pyrazinyl.
In one embodiment, Ar is optionally substituted imidazolyl.
In one embodiment, Ar is optionally substituted pyrazolyl.
In one embodiment, Ar is optionally substituted thiazolyl.
In one embodiment, Ar is optionally substituted oxazolyl.
In one embodiment, Ar is optionally substituted isoxazolyl.
In one embodiment, the compound is selected from the group consisting of:
(S)—N-(3-(6-amino-2-(difluoromethyl)-3,3-difluoro-2,3,4,5-tetrahydropyridin-2-yl)-4-fluorophenyl)-5-chloropicolinamide
(S)—N-(3-(6-amino-2-(difluoromethyl)-3,3-difluoro-2,3,4,5-tetrahydropyridin-2-yl)-4-fluorophenyl)-5-fluoropicolinamide
(S)—N-(3-(6-amino-2-(difluoromethyl)-3,3-difluoro-2,3,4,5-tetrahydropyridin-2-yl)-4-fluorophenyl)-5-methoxypyrazine-2-carboxamide
(S)—N-(3-(6-amino-2-(difluoromethyl)-3,3-difluoro-2,3,4,5-tetrahydropyridin-2-yl)-4-fluorophenyl)-2-methyloxazole-4-carboxamide
(S)—N-(3-(6-amino-2-(difluoromethyl)-3,3-difluoro-2,3,4,5-tetrahydropyridin-2-yl)-4-fluorophenyl)-5-methoxypicolinamide
(S)—N-(3-(6-amino-2-(difluoromethyl)-3,3-difluoro-2,3,4,5-tetrahydropyridin-2-yl)-4-fluorophenyl)-5-(difluoromethyl)pyrazine-2-carboxamide
(S)—N-(3-(6-amino-2-(difluoromethyl)-3,3-difluoro-2,3,4,5-tetrahydropyridin-2-yl)-4-fluorophenyl)-5-cyanopicolinamide
(S)—N-(3-(6-amino-2-(difluoromethyl)-3,3-difluoro-2,3,4,5-tetrahydropyridin-2-yl)-4-fluorophenyl)-4-methylthiazole-2-carboxamide
(S)—N-(3-(6-amino-2-(difluoromethyl)-3,3-difluoro-2,3,4,5-tetrahydropyridin-2-yl)-4-fluorophenyl)-5-methoxypyrimidine-2-carboxamide
(S)—N-(3-(6-amino-2-(difluoromethyl)-3,3-difluoro-2,3,4,5-tetrahydropyridin-2-yl)-4-fluorophenyl)-5-methoxy-3-methylpyrazine-2-carboxamide
(S)—N-(3-(6-amino-2-(difluoromethyl)-3,3-difluoro-2,3,4,5-tetrahydropyridin-2-yl)-4-fluorophenyl)-5-cyano-3-methylpicolinamide
(S)—N-(3-(6-amino-2-(difluoromethyl)-3,3-difluoro-2,3,4,5-tetrahydropyridin-2-yl)-4-fluorophenyl)-5-bromopicolinamide
(S)—N-(3-(6-amino-2-(difluoromethyl)-3,3-difluoro-2,3,4,5-tetrahydropyridin-2-yl)-4-fluorophenyl)-5-(methoxy-d3)picolinamide
(S)—N-(3-(6-amino-2-(difluoromethyl)-3,3-difluoro-2,3,4,5-tetrahydropyridin-2-yl)-4-fluorophenyl)-5-(methoxy-d3)pyrazine-2-carboxamide
or a pharmaceutically acceptable salt thereof.

A separate embodiment is directed to a pharmaceutical composition comprising a compound from the above list and a pharmaceutically acceptable carrier.

Another embodiment is directed to a method of treating a neurodegenerative or cognitive disorder comprising administering a therapeutically effective amount of a compound from the above list.

Yet another embodiment is directed to a use of a compound from the above list for the manufacture of a medicament for treating a neurodegenerative or cognitive disorder.

One embodiment is a compound from the above list for use in therapy.

Yet another embodiment is directed to a compound form the above list for use in the treatment of a neurodegenerative or cognitive disorder.

BRIEF DESCRIPTION OF THE FIGURE

FIG. 1: X-ray structure of (S)-5-bromo-N-(3-(2-(difluoromethyl)-3,3-difluoro-6-thioxopiperidin-2-yl)-4-fluorophenyl)picolinamide.

DETAILED DESCRIPTION OF THE INVENTION

The present invention is based on the discovery of the compounds of Formula I are inhibitors of BACE1, and as such, are useful for the treatment of related disorders. Certain aspects of the invention are explained in greater detail below but this description is not intended to be a detailed catalog of all the different ways in which the invention may be implemented, or all the features that may be added to the instant invention. Hence, the following specification is intended to illustrate some embodiments of the invention, and not to exhaustively specify all permutations, combinations and variations thereof.

As used herein, the term "$C_1$-$C_6$ alkyl" refers to a straight chained or branched saturated hydrocarbon having from one to six carbon atoms inclusive. Examples of $C_1$-$C_6$ alkyl include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "$C_1$-$C_3$ alkyl" refers to a straight chained or branched saturated hydrocarbon having from one to three carbon atoms inclusive. Examples of such substituents include, but are not limited to, methyl, ethyl and n-propyl.

Likewise, the term "$C_1$-$C_6$ alkoxy" refers to a straight chained or branched saturated alkoxy group having from one to six carbon atoms inclusive with the open valency on the oxygen. Examples of $C_1$-$C_6$ alkoxy include, but are not limited to, methoxy, ethoxy, n-butoxy, t-butoxy and n-hexyloxy. The "$C_1$-$C_6$ alkoxy" is optionally substituted with one or more fluorine atoms.

As used herein, the term "$C_1$-$C_6$ fluoroalkyl" refers to a straight chained or branched saturated hydrocarbon having from one to six carbon atoms inclusive substituted with one or more fluorine atoms. Examples of $C_1$-$C_6$ fluoroalkyl include, but are not limited to, trifluoromethyl, pentafluoroethyl, 1 fluoroethyl, monofluoromethyl, difluoromethyl, 1,2-difluoroethyl and 3,4 difluorohexyl. Similarly, the term "$C_1$-$C_3$ fluoroalkyl" refers to a straight chained or branched saturated hydrocarbon having from one to three carbon atoms inclusive substituted with one or more fluorine atoms per carbon atom.

The term "halogen" refers to fluorine, chlorine, bromine and iodine.

The term "$C_2$-$C_6$ alkenyl" refers to a branched or unbranched alkenyl group having from two to six carbon atoms and one double bond, including but not limited to ethenyl, propenyl, and butenyl. The term "$C_2$-$C_6$ alkynyl" shall mean a branched or unbranched alkynyl group having from two to six carbon atoms and one triple bond, including but not limited to ethynyl, propenyl and butynyl.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "effective amount" is the amount of a compound of the present invention in the combination sufficient to cause the intended biological effect.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

The present invention is based on the discovery that compounds of Formula I are inhibitors of BACE1, and as such, are useful for the treatment of disorders which pathological characteristics comprise β-amyloid deposits and neurofibrillary tangles, such as neurodegenerative or cognitive disorders.

The compounds of the present invention are, as discussed above, expected to be useful in the treatment of Alzheimer's disease due to their effects on β-amyloid deposits and neurofibrillary tangles. This includes familial Alzheimer's disease where patients carry mutations on specific genes intimately involved in the production of Aβ peptide. It is, however, important to note that aggregates of Aβ peptide is not limited to familial Alzheimer's disease but is similarly an important pathophysiological characteristics of the more common sporadic Alzheimer's disease [*Mol Cell Neurosci*, 66, 3-11, 2015].

The compounds of the present invention are also believed to be useful in the treatment of early-stage Alzheimer's disease, i.e. disease stages where the biological and structural changes have started but the clinical manifestations of the disease have not yet become evident or are not yet well developed. Early-stage Alzheimer's disease may, in fact, start years before any clinical manifestation of the disease becomes manifest. Early-stage Alzheimer's disease includes prodromal Alzheimer's disease, preclinical Alzheimer's disease and mild cognitive impairment. Although mild cognitive impairment may be unrelated to Alzheimer's disease it is often a transitional stage to Alzheimer's disease or due to Alzheimer's disease. Preclinical and prodromal Alzheimer's disease are asymptomatic stages, and they are typically diagnosed by the presence of Alzheimer's disease related biomarkers. In this context the compounds of the present invention are believed to be useful in slowing down the progression of early-stage Alzheimer's disease, such as mild cognitive impairment to Alzheimer's disease. The compounds of the present invention are also believed to be useful in the treatment of memory loss, attention deficits and dementia associated with Alzheimer's disease.

Other diseases, in addition to the continuum of Alzheimer's disease, are characterized by β-amyloid deposits and neurofibrillary tangles. This includes e.g. Trisomy 21 also known as Down's syndrome. Patients suffering from Down's syndrome have an extra chromosome 21 which chromosome contains the gene for the amyloid precursor protein (APP). The extra chromosome 21 leads to overexpression of APP, which leads to increased levels of Aβ peptide, which eventually causes the markedly increased risk of developing Alzheimer's disease seen in Down's syndrome patients [*Alzheimer's & Dementia*, 11, 700-709, 201]. Cerebral amyloid angiopathy is also characterized by β-amyloid deposits and neurofibrillary tangles in blood vessels of the central nervous system [*Pharmacol Reports*, 67, 195-203, 2015] and is as such expected to be treatable with compounds of the present invention.

In one embodiment, the present invention provides a method of treating a disease selected from Alzheimer's disease (familial or sporadic), preclinical Alzheimer's disease, prodromal Alzheimer's disease, mild cognitive impairment, Down's syndrome and cerebral amyloid angiopathy, the method comprising the administration of a therapeutically effective amount of a compound of Formula I or a pharmaceutically acceptable salt thereof to a patient in need thereof.

The present invention further provides a method of inhibiting BACE1 in a patient comprising administering to a patient in need thereof a therapeutically effective amount of a compound of Formula I or a pharmaceutically acceptable salt thereof.

The present invention also provides a method of inhibiting β-secretase mediated cleavage of amyloid precursor protein comprising administering to a patient in need of such treatment a therapeutically effective amount a compound of Formula I or a pharmaceutically acceptable salt thereof. In further embodiments, the present invention provides the use of a compound of Formula I or a pharmaceutically acceptable salt thereof for the manufacture of a medicament for the treatment of disease selected from Alzheimer's disease (familial or sporadic), preclinical Alzheimer's disease, prodromal Alzheimer's disease, mild cognitive impairment, Down's syndrome or cerebral amyloid angiopathy.

The present invention also provides the use of a compound of Formula I or a pharmaceutically acceptable salt thereof for the manufacture of a medicament for the inhibition of BACE1. The present invention further provides the use of a compound of Formula I or a pharmaceutically acceptable salt thereof for the manufacture of a medicament for the inhibition of production or accumulation of Aβ peptide.

In one embodiment, the present invention provides a compound of Formula I or a pharmaceutically acceptable salt thereof for use in a method for the treatment of a disease selected form Alzheimer's disease (familial or sporadic), preclinical Alzheimer's disease, prodromal Alzheimer's disease, mild cognitive impairment, Down's syndrome or cerebral amyloid angiopathy.

In one embodiment, the present invention relates to a compound of Formula I or a pharmaceutically acceptable salt thereof for use in a method for inhibiting of BACE1 or in a method for inhibiting of production or accumulation of Aβ peptide.

In a further embodiment, the invention provides a pharmaceutical formulation adapted for any of the above treatments and uses.

In one embodiment, a mammal is a human.

In one embodiment, the patient is a human patient.

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., *J. Pharm. Sci.*, 1977, 66, 2.

Furthermore, the compounds of this invention may exist in unsolvated as well as in solvated forms with pharmaceutically acceptable solvents such as water, ethanol and the like.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention.

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

The present invention further provides a pharmaceutical composition comprising a therapeutically effective amount of a compound of Formula I or a pharmaceutically acceptable salt thereof and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22$^{th}$ Edition, Gennaro, Ed., Mack Publishing Co., Easton, Pa., 2013.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs. Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.01 to about 100 mg/kg body weight per day.

The compounds of this invention are generally utilized as the free base or as a pharmaceutically acceptable salt thereof. A pharmaceutically acceptable salt of a compound of Formula I is prepared e.g. in a conventional manner by treating a solution or suspension of a free base of Formula I with a molar equivalent of a pharmaceutically acceptable acid. Representative examples of suitable organic and inorganic acids are described above.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of Formula I or a pharmaceutically acceptable salt thereof and a pharmaceutically acceptable carrier are readily administered in a variety of dosage forms suitable for the disclosed routes of administration. The formulations may conveniently be presented in unit dosage form by methods known in the art of pharmacy.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

EXPERIMENTAL SECTION

The compounds of the present invention of the general formula I, wherein $R^1$ and Ar are as defined above can be prepared by the methods outlined in the following reaction schemes 1-4 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

For example, Scheme 2 describe the use of selective protecting groups during the synthesis of the compounds of the invention. One skilled in the art would be able to select the appropriate protecting group for a particular reaction. Moreover, it may be necessary to incorporate protection and deprotection strategies for substituents such as amino, amido, keto and hydroxyl groups in the synthetic methods described below to synthesize the compounds of Formula I. Methods for protection and deprotection of such groups are well known in the art, and may be found in T. Green, et al., Protective Groups in Organic Synthesis, 1991, $2^{nd}$ Edition, John Wiley & Sons, New York.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers.

Analytical LC-MS data was obtained using the following methods.

Method A:
LC-MS was run on Waters Acquity UPLC-MS consisting of Waters Acquity including column manager, binary solvent manager, sample organizer, PDA detector (operating at 254 nM), ELS detector, and SQ-MS equipped with APPI-source operating in positive ion mode.
LC-conditions: The column was Acquity UPLC BEH C18 1.7 µm; 2.1×150 mm operating at 60° C. with 0.6 ml/minutes of a binary gradient consisting of water+0.05% trifluoroacetic acid (A) and acetonitrile+5% water+0.03% trifluoroacetic acid (B). Gradient: 0.00 min: 10% B; 3.00 min: 99.9% B; 3.01 min: 10% B; 3.60 min: 10% B. Total run time: 3.60 min.

Method B:
LC-MS was run on Waters Acquity UPLC-MS consisting of Waters Acquity including column manager, binary solvent manager, sample organizer, PDA detector (operating at 254 nm), ELS detector, and TQ-MS equipped with APPI-source operating in positive ion mode.
LC-conditions: The column was Acquity UPLC BEH C18 1.7 µm ; 2.1×50 mm operating at 60° C. with 1.2 ml/minutes of a binary gradient consisting of water+0.05% trifluoroacetic acid (A) and acetonitrile+5% water+0.05% trifluoroacetic acid (B). Gradient: 0.00 min: 10% B; 1.00 min: 100% B; 1.01 min: 10% B; 1.15 min: 10% B. Total run time: 1.15 min.

$^1$H NMR spectra were recorded at 600 MHz on a Bruker Avance AV-III-600 instrument or at 400 MHz on a Bruker Avance AV-III-400 instrument or a Varian 400 instrument. Chemical shift values are expressed in ppm-values relative. The following abbreviations are used for multiplicity of NMR signals: s=singlet, d=doublet, t=triplet, q=quartet, dd=double doublet, ddd=double double doublet, dt=double triplet, br=broad, and m=multiplet.

As an example and wherein $R^1$ is fluorine in the ortho position of the phenyl ring, compounds of the general formula IV may be prepared as shown in Scheme 1.

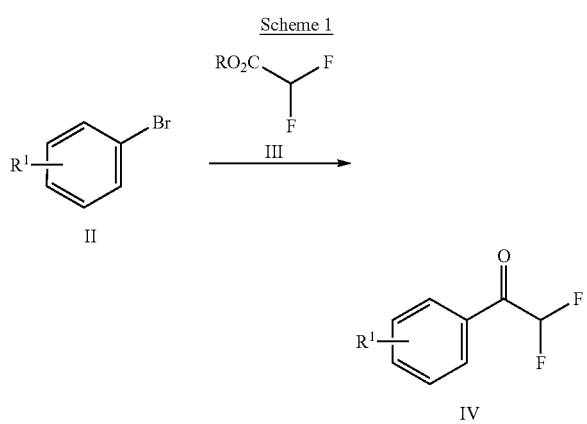

where $R^1$ is as defined under formula I and R is an alkyl group such as methyl or ethyl. Compounds of the general formula IV (Scheme 1) may be prepared by reacting compounds of the general formula II with a halogen-metal exchange reagent such as butyllithium followed by addition to an ester of general formula III.

As an example and wherein $R^1$ is fluorine in the ortho position of the phenyl ring, compound of the general formula XVI may be prepared as shown in Scheme 2.

Scheme 2

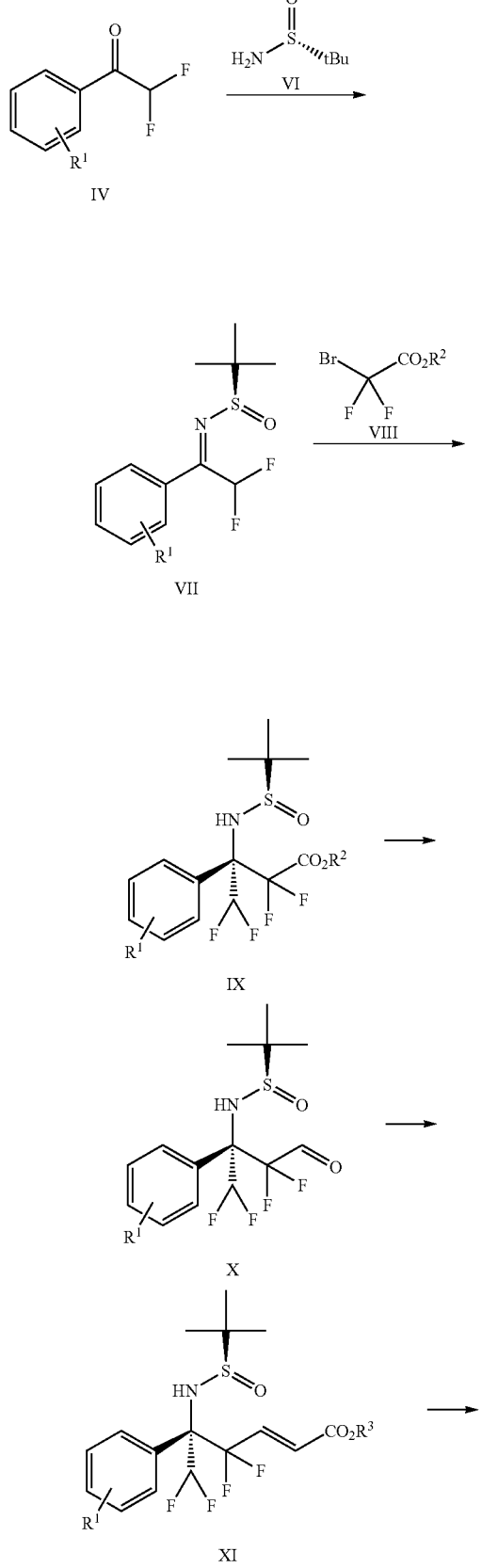

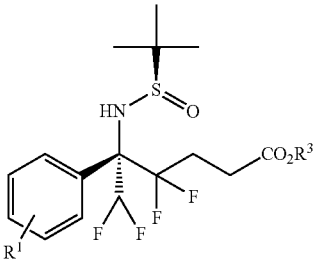

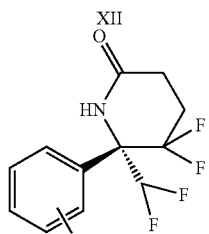

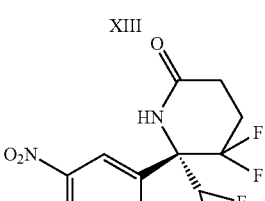

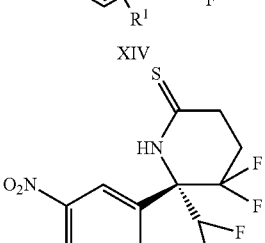

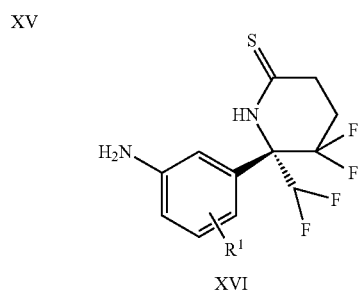

where $R^2$ and $R^3$ are an alkyl group such as methyl or ethyl.

Compounds of the general formula VII (Scheme 2) may be prepared by reacting compounds of the general formula IV with a sulfinamide such as VI in the presence of a Lewis acid/drying agent such as titanium tetraethoxide. Treatment of compounds of the general formula VII with compounds of the general formula VIII such as ethyl bromodifluoroacetate in the presence of Zn powder or in the presence of diethyl zinc and tris(triphenylphosphine)rhodium(I) chloride gives compounds of the general formula IX. Compounds of the general formula X are obtained from compounds of the general formula IX by treatment with a reducing agent such as diisobutylaluminium hydride. In some cases compound X might be in equilibrium with the hydrate form. Treatment of compounds of the general formula X with conditions such as methyl 2-(dimethoxyphosphoryl)-acetate in the presence of lithium chloride and a base such as N,N-diisopropylethylamine gives compounds of the general formula XI. Compounds of the general formula XII are obtained by hydrogenation of compounds of the general formula XI in the precense of a catalyst such as palladium on carbon. Compounds of the general formula XIII are obtained by treatment of compounds of the general formula XII with an acid such as hydrochloric acid in methanol followed by treatment with potassium carbonate in methanol or heating in a solvent such as toluene. Compounds of the general formula XIII can be nitrated using nitric acid to give compounds of the general formula XIV. Treatment of compounds of the general formula XIV with a reagent such as Lawesson's reagent (2,4-bis(4-methoxyphenyl)-1,3,2,4-dithiadiphosphetane-2,4-disulfide) gives compounds of the general formula XV. Reduction of the nitro group of compounds of the general formula XV gives compounds of the general formula XVI.

Compounds of the general formula XIV may also be prepared as shown in Scheme 3. Starting from nitro substituted acetophenones of general formula IVb, compounds of the general formula XIb may be prepared as described in Scheme 2. Compounds of the general formula XIIb are obtained by hydrogenation of compounds of the general formula XIb in the presence of a catalyst such as palladium on carbon. Compounds of the general formula XIV may be prepared as described Scheme 2 for the preparation of compounds of the general formula XIII from compounds of the general formula XII. Protection of the aniline moiety of compounds of the general formula XIV gives compounds of the general formula XIVb. Treatment of compounds of the general formula XIVb with a reagent such as Lawesson's reagent (2,4-bis(4-methoxyphenyl)-1,3,2,4-dithiadiphosphetane-2,4-disulfide) followed by deprotection of the aniline moiety gives compounds of the general formula XVI.

Scheme 3

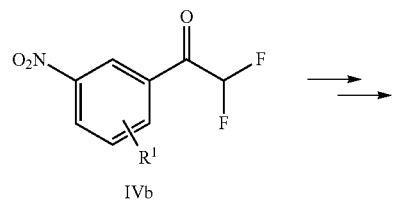

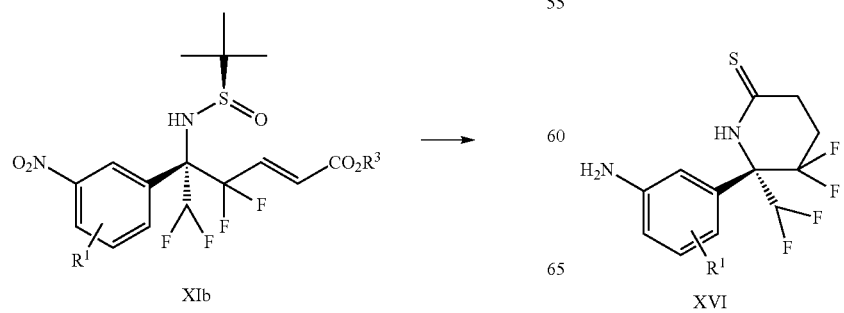

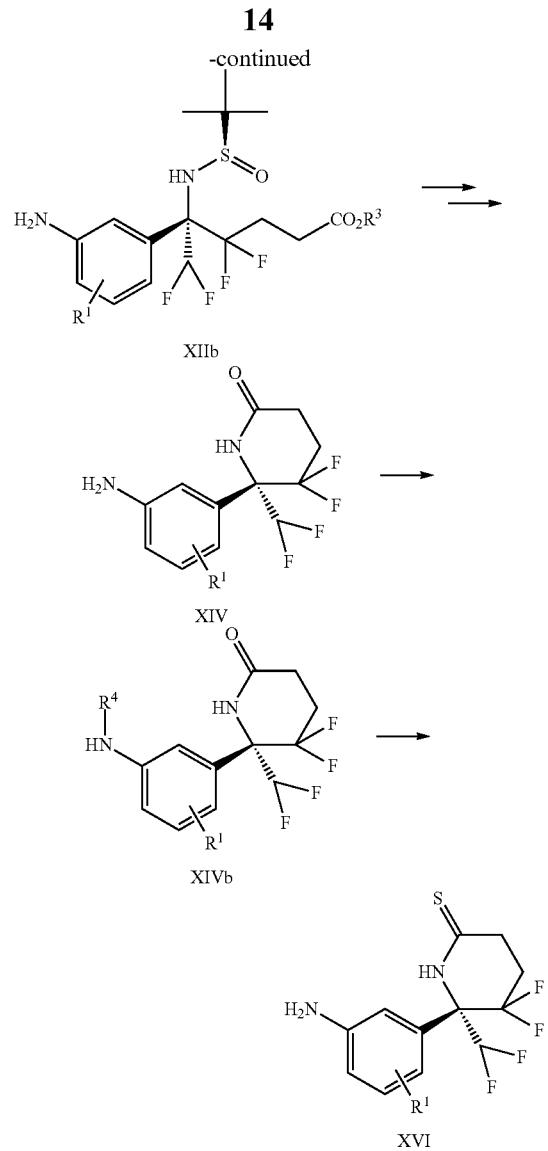

where $R^1$ is as defined under formula I and $R^3$ is an alkyl group such as methyl or ethyl Compounds of the general formula I may be prepared as shown in Scheme 4.

Scheme 4

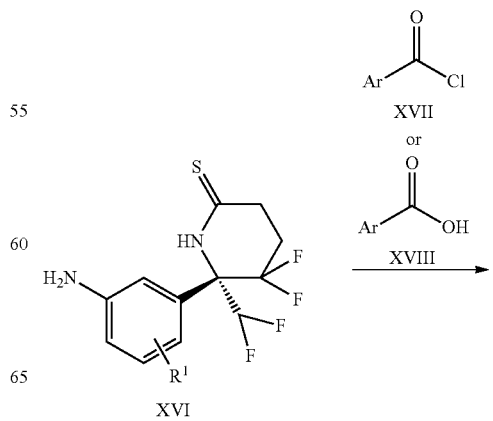

-continued

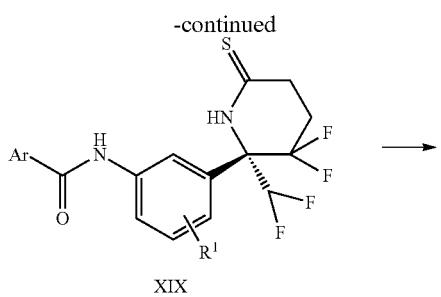

XIX

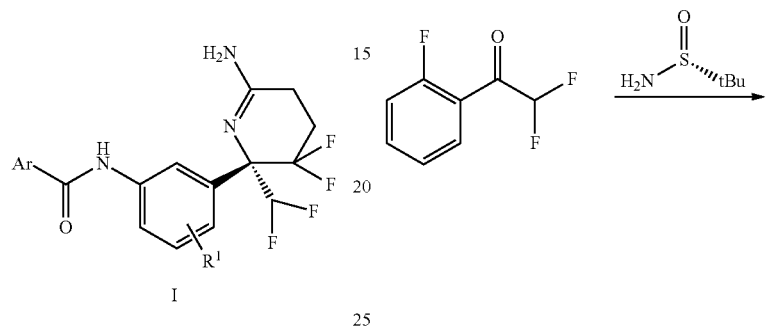

I where R¹ and Ar are as defined under formula I.

Compounds of the general formula XIX may be prepared by reacting compounds of the general formula XVI with a carboxylic acid chloride of general formula XVII or by reaction with a carboxylic acid of general formula XVIII using procedures known to chemists skilled in the art. Treatment of compounds of the general formula XIX with ammonia gives compounds of the general formula I. In some cases, the addition of an oxidizing reagent such as tert-butyl hydroperoxide might be necessary to facilitate the reaction.

PREPARATION OF INTERMEDIATES

INTERMEDIATE:
2,2-difluoro-1-(2-fluorophenyl)ethan-1-one

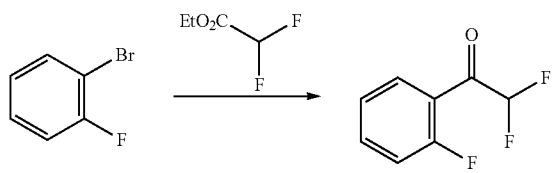 [SMILES: Fc1ccccc1Br ; CCOC(=O)C(F)F ; O=C(c1ccccc1F)C(F)F]

To a solution of 1-bromo-2-fluorobenzene (10.00 g, 57.14 mmol) in THF (200 mL) was added n-butyllithium (2.5 M, 24.00 mL) drop-wise at −78° C. over a period of 15 minutes under $N_2$. The mixture was stirred at −78° C. for 30 min. Ethyl 2,2-difluoroacetate (10.64 g, 85.71 mmol) was added dropwise at −78° C. and stirred for 2 hours at −78° C. TLC showed no starting material remained. Saturated aqueous $NH_4Cl$ (15 mL) was added dropwise at −78° C. The reaction mixture was warmed to 25° C., extracted with ethyl acetate (100 mL, three times). The combined organic phases were washed with brine (30 mL), dried over anhydrous $Na_2SO_4$, filtered and concentrated in vacuo. The residue was purified by column chromatography on silica gel (petroleum ether: ethyl acetate=95:5) to afford 2,2-difluoro-1-(2-fluorophenyl)ethan-1-one (5.60 g, 47.8% yield, 85% purity). ¹H NMR ($CDCl_3$, 400 MHz): δ 7.99-7.95 (m, 1H), 7.70-7.64 (m, 1H), 7.33 (t, J=7.6 Hz 2H), 7.24 (dd, J=10.8, 8.4 Hz, 1H), 6.59-6.32 (m, 1H).

INTERMEDIATE: (R)—N-(2,2-difluoro-1-(2-fluorophenyl)ethylidene)-2-methylpropane-2-sulfinamide

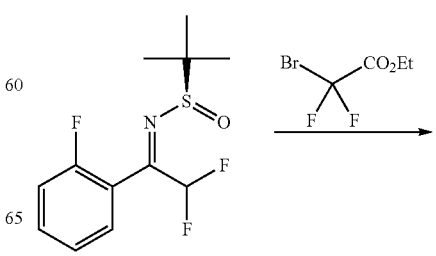

To a solution of 2,2-difluoro-1-(2-fluorophenyeethan-1-one (5.60 g, 32.16 mmol) and (R)-2-methyl-propane-2-sulfinamide (5.07 g, 41.81 mmol) in THF (110 mL), was added tetraethoxytitanium (14.67 g, 64.32 mmol) in one portion at 26° C. The yellow solution was stirred at 80° C. for 2.5 hr. TLC (petroleum ether:ethyl acetate=3:1) showed no starting material remained. The mixture was cooled to 26° C. Water (10 mL) was added to the mixture and it was filtered and extracted with ethyl acetate (60 mL, three times). The organic layer was washed with brine, dried over $Na_2SO_4$, filtered and concentrated and then purified by column chromatography on silica gel (petroleum ether:ethyl acetate=91:9) to afford (R)—N-2,2-difluoro-1-(2-fluorophenyl)ethylidene)-2-methylpropane-2-sulfinamide (5.60 g, 61.6% yield, 98.1% purity).

INTERMEDIATE: ethyl (S)-3-(((R)-tert-butylsulfinyl)amino)-2,2,4,4-tetrafluoro-3-(2-fluoro-phenyl)butanoate

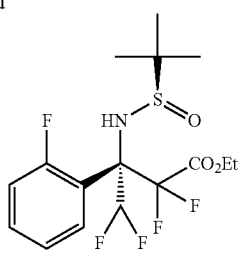

To a solution of (R)—N-(2,2-difluoro-1-(2-fluorophenyeethylidene)-2-methylpropane-2-sulfinamide (4.60 g, 16.6 mmol), ethyl 2-bromo-2,2-difluoro-acetate (6.73 g, 33.18 mmol) and Rh(PPh$_3$)$_3$Cl (469 mg, 498 μmol) in THF (90 mL) was added a solution of diethyl zinc (1 M in THF, 33 mL) dropwise at −78° C. over a period of 20 minutes under Ar, during which the temperature was maintained below −65° C. The reaction mixture was warmed to 0° C. over a period of 10 minutes and stirred at 0° C. for 2 hours. TLC (petroleum ether/ethyl acetate=3:1) showed the starting material was consumed completely. The dark red solution was quenched by water (40 mL) and then filtered. The filtrate was extracted with ethyl acetate (100 mL, twice). The combined organic phases were washed with saturated brine (30 mL), dried over anhydrous Na$_2$SO$_4$, filtered and concentrated in vacuo. The crude product was purified by column chromatography on silica gel (petroleum ether/ethyl acetate=4:1) to give ethyl (S)-3-(((R)-tert-butylsulfinyeamino)-2,2,4,4-tetrafluoro-3-(2-fluorophenyl)butanoate (4.26 g, 62.1% yield). $^1$H NMR (DMSO-d6, 400 MHz): δ 7.65-7.31 (m, 1H), 7.49-7.44 (m, 1H), 7.23-7.12 (m, 2H), 6.93-6.66 (m, 1H), 5.00 (s, 1H), 4.39-4.29 (m, 2H), 1.39 (s, 9H), 1.32 (t, J=8.0 Hz, 3H).

INTERMEDIATE: (R)-2-methyl-N-((S)-1,1,3,3-tetrafluoro-2-(2-fluorophenyl)-4-oxobutan-2-yl)-propane-2-sulfinamide

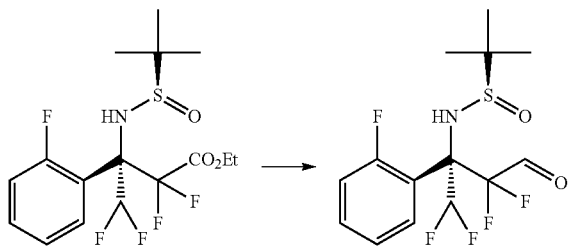

To a solution of ethyl (S)-3-(((R)-tert-butylsulfinyl) amino)-2,2,4,4-tetrafluoro-3-(2-fluorophenyl)-butanoate (3.20 g, 7.97 mmol) in dry THF (35 mL) was added dropwise a solution of DIBAL-H (diisobutylaluminium hydride) in toluene (1.0 M, 16 mL, 16 mmol) at −78° C. under N$_2$. The mixture was stirred at −78° C. for 2 hours. The reaction was quenched carefully with methanol (3 mL) at −78° C. Then water (20 mL) and ethyl acetate (200 mL) were added and the mixture was warmed to 25° C. The mixture was aged for 30 minutes. The resulting mixture was filtered through a Celite pad. The organic layer was washed with brine and dried over Na$_2$SO$_4$. The organic layer was concentrated to give crude product (R)-2-methyl-N—((S)-1,1,3,3-tetrafluoro-2-(2-fluorophenyl)-4-oxobutan-2-yl)propane-2-sulfinamide, which was used immediately in the next step without further purification.

INTERMEDIATE: ethyl (S)-5-(((R)-tert-butylsulfinyl)amino)-4,4,6,6-tetrafluoro-5-(2-fluorophenyl)-hex-2-enoate

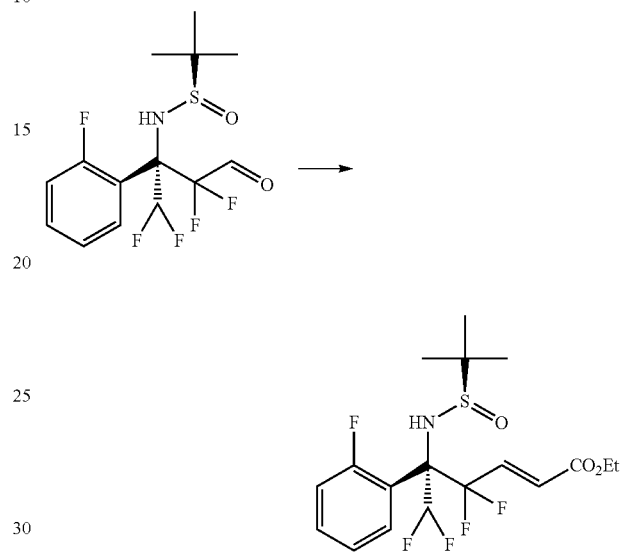

To a stirred suspension of LiCl (405 mg, 9.56 mmol) in acetonitrile (30 mL) under N$_2$ were added ethyl 2-diethoxy-phosphorylacetate (2.14 g, 9.56 mmol) and DIPEA (N,N-diisopropylethylamine) (2.06 g, 15.94 mmol) at 0° C. After 20 min, (R)-2-methyl-N-((S)-1,1,3,3-tetrafluoro-2-(2-fluorophenyl)-4-oxo-butan-2-yl)propane-2-sulfinamide (2.85 g, 7.97 mmol) in acetonitrile (10 mL) was added dropwise to the mixture at 0° C. and the mixture was stirred at 25° C. for 17.5 hours. The reaction mixture was concentrated to remove acetonitrile, water (50 ml) was added and extracted with ethyl acetate (200 ml). The organic layer was dried and evaporated. The crude product was purified by column chromatography (petrolium ether:ethyl acetate=5:1 to 4:1) to afford ethyl (S)-5-(((R)-tert-butylsulfiny/amino)-4,4,6,6-tetrafluoro-5-(2-fluorophenyl)hex-2-enoate (1.77 g, 46.8% yield).

INTERMEDIATE: ethyl (S)-5-(((R)-tert-butylsulfinyl)amino)-4,4,6,6-tetrafluoro-5-(2-fluorophenyl)-hexanoate

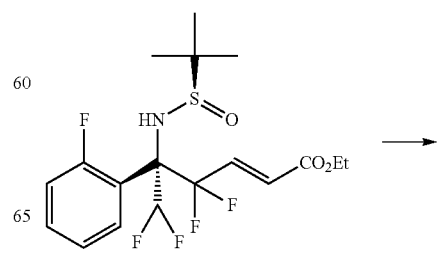

-continued

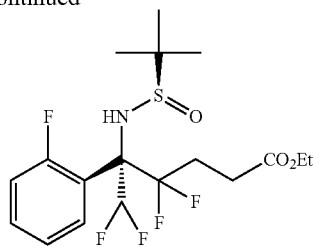

To a solution of ethyl (S)-5-(((R)-tert-butylsulfinyl)amino)-4,4,6,6-tetrafluoro-5-(2-fluorophenyl)hex-2-enoate (1.77 g, 4.28 mmol) in ethyl acetate (100 mL) was added Pd/C (400 mg, 10%). The black suspension was stirred at 25° C. for 18 hours under 45-50 psi $H_2$. It was filtrated and concentrated to give ethyl (S)-5-(((R)-tert-butylsulfinyl)amino)-4,4,6,6-tetrafluoro-5-(2-fluorophenyl)hexanoate (1.70 g, 95.5% yield) which was used in the next step immediately without further purification.

INTERMEDIATE: (S)-6-(difluoromethyl)-5,5-difluoro-6-(2-fluorophenyl)piperidin-2-one

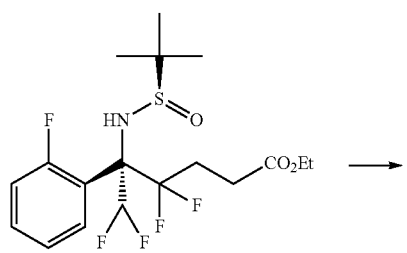

To a solution of ethyl (S)-5-(((R)-tert-butylsulfinyl)amino)-4,4,6,6-tetrafluoro-5-(2-fluorophenyl)-hexanoate (1.70 g, 4.09 mmol) in dichloromethane (15 mL) was added HCl/MeOH (4 M, 17 mL). The colorless solution was stirred at 25° C. for 1 hour. TLC analysis showed no starting material was left. The mixture was concentrated and the residue was dissolved in toluene. The resulting mixture was concentrated again to give 1.5 g of a colorless oil. This oil was dissolved in toluene (30 mL) and was stirred at 100° C. for 18 hours. After the mixture was cooled to 25° C., it was concentrated to give the crude product which was purified by flash chromatography on silica gel (petroleum ether:ethyl acetate=2:1) to give (S)-6-(difluoromethyl)-5,5-difluoro-6-(2-fluorophenyl)piperidin-2-one (880 mg, 3.15 mmol, 73% yield).

INTERMEDIATE: (S)-6-(difluoromethyl)-5,5-difluoro-6-(2-fluoro-5-nitrophenyl)piperidin-2-one

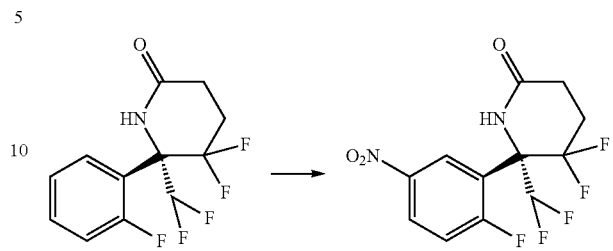

(S)-6-(difluoromethyl)-5,5-difluoro-6-(2-fluorophenyl)piperidin-2-one (880 mg, 3.15 mmol) was suspended in trifluoroacetic acid (2.55 mL). The mixture was cooled to 0° C. and concentrated $H_2SO_4$ (2.46 g, 24.3 mmol) was added. Then, $HNO_3$ (661.61 mg, 6.30 mmol) was added dropwise. After 2 hours of stirring at 25 ° C., the reaction mixture was poured onto 100 g ice and basified to pH>11 using 5 M NaOH (aq). The suspension was extracted with ethyl acetate (150 mL). The phases were separated and the aqueous layer was extracted with ethyl acetate (2×70 mL). The combined organic phases were washed with a solution of saturated aqueous $NH_4Cl$ (30 mL) and water (30 mL), dried over $MgSO_4$, filtered, and concentrated under reduced pressure to afford (S)-6-(difluoromethyl)-5,5-difluoro-6-(2-fluoro-5-nitrophenyl)piperidin-2-one (1.00 g, crude).

INTERMEDIATE: (S)-6-(difluoromethyl)-5,5-difluoro-6-(2-fluoro-5-nitrophenyl)piperidine-2-thione

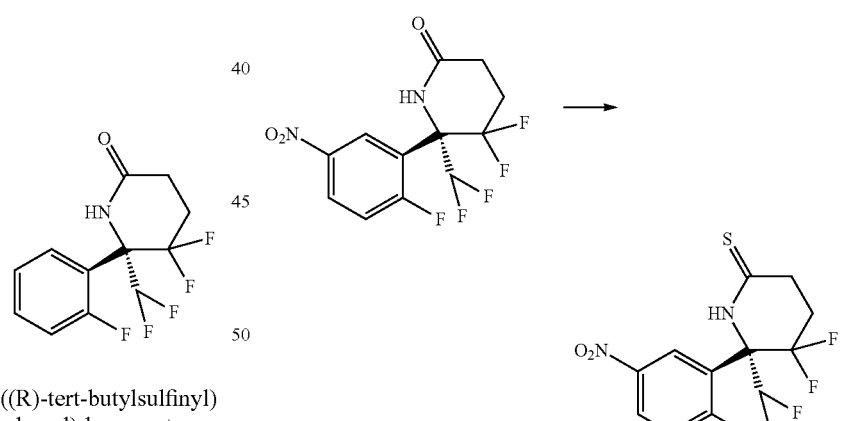

To a solution of (S)-6-(difluoromethyl)-5,5-difluoro-6-(2-fluoro-5-nitrophenyl)piperidin-2-one (1.00 g, 3.08 mmol) in toluene (5 mL) was added Lawesson's reagent (2,4-bis(4-methoxyphenyl)-1,3,2,4-dithia-diphosphetane-2,4-disulfide) (686 mg, 1.70 mmol). The mixture was stirred at 100° C. for 2 hours. TLC analysis showed no starting material remained. The mixture was concentrated and the crude product was purified by flash chromatography on silica gel (petroleum ether:ethyl acetate=5:1) to give (S)-6-(difluoromethyl)-5,5-difluoro-6-(2-fluoro-5-nitrophenyl)piperidine-2-thione (1.00 g, 2.94 mmol, 95.4% yield).

INTERMEDIATE: (S)-6-(5-amino-2-fluorophenyl)-6-(difluoromethyl)-5,5-difluoropiperidine-2-thione

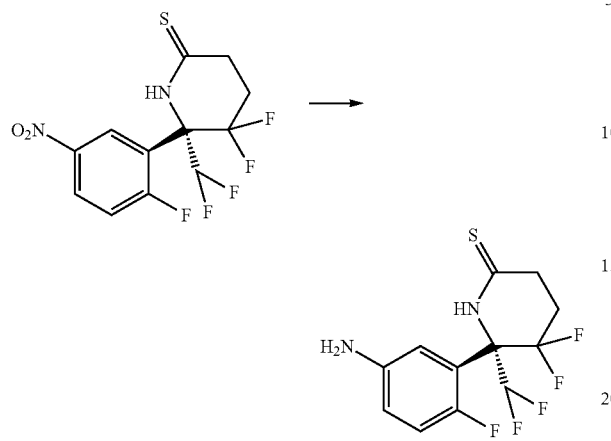

To a suspension of (S)-6-(difluoromethyl)-5,5-difluoro-6-(2-fluoro-5-nitrophenyl)piperidine-2-thione (1.00 g, 2.94 mmol) in ethanol (15 mL) and water (4 mL) was added iron powder (821 mg, 145 mmol) and NH$_4$Cl (786 mg, 14.7 mmol, 5.0 Eq). The black mixture was stirred at 60° C. for 18 hours. After the reaction mixture was cooled to 25 ° C., the crude product was filtered and the residue was washed with ethanol (100 mL). The combined filtrates were concentrated and the resulting solid was dispersed in ethyl acetate (100 mL). The mixture was filtered and the filtrate was washed with water (30 mL), brine (20 mL) and concentrated. The crude product was purified by flash chromatography on silica (petroleum ether:ethyl acetate=3:1~2:1) to give (S)-6-(5-amino-2-fluorophenyl)-6-(difluoromethyl)-5,5-difluoropiperidine-2-thione (819 mg, 2.51 mmol, 85.3% yield). $^1$H NMR (DMSO-d6, 400 MHz): δ 10.97 (s, 1H), 7.03-6.90 (m, 2H), 6.64-6.55 (m, 2H), 5.19 (s, 2H), 3.19-3.15 (m, 1H), 3.03-2.94 (m, 1H), 2.35-2.24 (m, 2H).

INTERMEDIATE: methyl-d$_3$-5-(methoxy-d$_3$)pyrazine-2-carboxylate

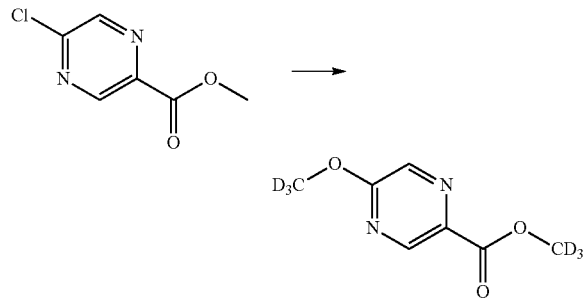

Sodium (0.094 g, 4.10 mmol) was added in small portions methanol-d$_4$ (2.94 ml) and the reaction mixture was stirred until all sodium has reacted. The soultion was the added to another soultion of methyl-5-chloropyrazine-2-carboxylate (0.6 g, 3.48 mmol) in methanol-d$_4$ (0.98 ml). The reaction mixture was stirred for 1.5 hours at room temperature. The reaction mixture was concentrated in vacuo. 2 ml of water was added. The mixture was extracted with ethyl acetate. The organic phase was washed with brine, dried over MgSO$_4$ and concentrated in vacuo to give methyl-d$_3$-5-(methoxy-d$_3$)pyrazine-2-carboxylate.

INTERMEDIATE: methyl 5-(methoxy-d$_3$)picolinate

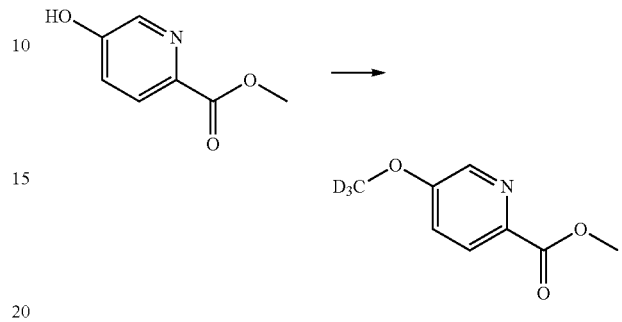

Methyl 5-hydroxypicolinate (2.88 g, 18.8 mmol) was dissolved in dimethylformamide (108 ml) under argon. Potassium carbonate (7.20 g, 52.1 mmol) was added and the orange suspension was stirred for 45 minutes at room temperature. Iodomethane-d$_3$ (1.41 ml, 22.6 mmol) was added. The reaction mixture was stirred for 2 hours. Water was added. The mixture was extracted with ethyl acetate. The organic phase was washed with brine, dried over MgSO$_4$ and concentrated in vacuo and purified by column chromatography on silica gel (heptane: ethyl acetate) to give methyl 5-(methoxy-d$_3$)picolinate.

PREPARATION OF THE COMPOUNDS OF THE INVENTION

EXAMPLE 1

(S)-N-(3-(6-amino-2-(difluoromethyl)-3,3-difluoro-2,3,4,5-tetrahydropyridin-2-yl)-4-fluorophenyl)-5-chloropicolinamide (Compound 1)

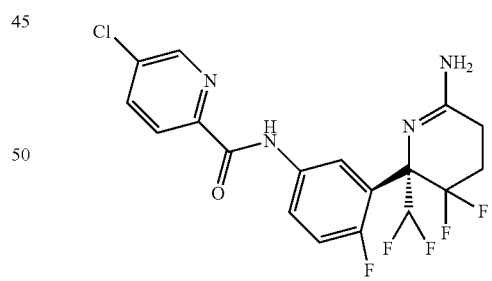

5-chloropicolinic acid (19 mg, 0.12 mmol) and HATU (1-[bis(dimethylamino)methylene]-1H-1,2,3-triazolo[4,5-b]pyridinium 3-oxid hexafluorophosphate) (67.4 mg, 0.177 mmol) was dissolved DMF (1 mL). The reaction mixture was stirred for 5 minutes. Then (S)-6-(5-amino-2-fluorophenyl)-6-(difluoromethyl)-5,5-difluoropiperidine-2-thione (25mg, 0.081 mmol) and DIPEA (N,-di-isopropyl ethylamine) (52 mg, 0.07 ml, 0.4 mmol) were added. The reaction mixture was stirred for 1 hour at room temperature. Satureted aqueous NH$_4$Cl was added and the mixture was extracted with ethyl acetate. The combined organic phases were washed with brine, dried over MgSO$_4$, filtered, and concentrated under reduced pressure Ammonia in methanol (7M, 2mL) was added and the reaction mixture was stirred at 55° C. in a sealed vial overnight. The reaction mixture was concentrated under reduced pressure. The crude product was purified by flash chromatography on silica (heptane:ethyl acetate). The product was dissolved in ethyl acetate and washed 5 times with satureted aqueous NaHCO3/water to remove thiourea byproducts. The combined organic phases were washed with brine, dried over MgSO$_4$, filtered, and concentrated under reduced pressure to give (S)-N-(3-(6-amino-2-(difluoromethyl)-3,3-difluoro-2,3,4,5-tetrahydropyridin-2-yl)-4-fluorophenyl)-5-chloropicolinamide. $^1$H NMR (DMSO-d6, 600 MHz): δ 10.78 (s, 1H), 8.79 (dt, J=2.4, 1.1 Hz, 1H), 8.20 (dd, J=8.4, 2.4 Hz, 1H), 8.16 (dd, J=8.4, 0.7 Hz, 1H), 7.96-7.90 (m, 1H), 7.88 (dd, J=6.8, 2.7 Hz, 1H), 7.20 (dd, J=11.6, 8.8 Hz, 1H), 6.74 (t, J=55.2 Hz, 1H), 6.38 (s, 2H), 2.51 (dt, J=3.7, 1.8 Hz, 2H), 2.19-1.98 (m, 2H).

LC-MS (m/z) 433 (MH$^+$); t$_R$=0.53 minutes (Method A)

EXAMPLE 2

(S)-N-(3-(6-amino-2-(difluoromethyl)-3,3-difluoro-2,3,4,5-tetrahydropyridin-2-yl)-4-fluorophenyl)-5-fluoropicolinamide (Compound 2)

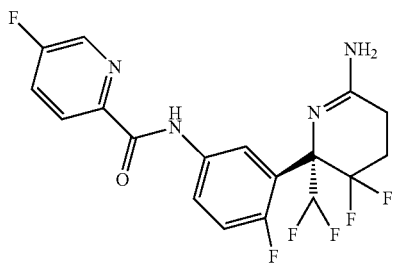

Prepared as in example 1 from (S)-6-(5-amino-2-fluorophenyl)-6-(difluoromethyl)-5,5-difluoropiperidine-2-thione and 5-fluoropicolinic acid.

$^1$H NMR (600 MHz, DMSO) δ 10.72 (s, 1H), 8.74 (d, J=2.8 Hz, 1H), 8.24 (dd, J=8.7, 4.6 Hz, 1H), 7.99 (td, J=8.7, 2.8 Hz, 1H), 7.95-7.91 (m, 1H), 7.88 (dd, J=6.8, 2.7 Hz, 1H), 7.20 (dd, J=11.6, 8.8 Hz, 1H), 6.74 (t, J=55.2 Hz, 1H), 6.38 (s, 2H), 2.56-2.50 (m, 2H), 2.22-1.98 (m, 2H).

LC-MS (m/z) 417.1 (MH$^+$); t$_R$=0.49 minutes (Method A)

EXAMPLE 3

(S)-N-(3-(6-amino-2-(difluor omethyl)-3 ,3-difluoro-2,3,4,5-tetrahydropyridin-2-yl-4-fluorophenyl)-5-methoxypyrazine-2-carboxamide (Compound 3)

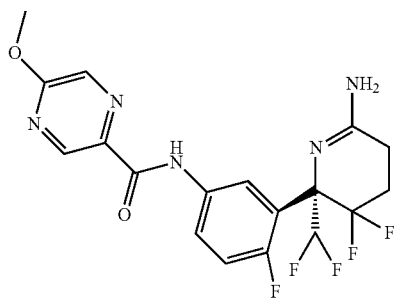

Prepared as in example 1 from (S)-6-(5-amino-2-fluorophenyl)-6-(difluoromethyl)-5,5-difluoropiperidine-2-thione and 5-methoxypyrazine-2-carboxylic acid. $^1$H NMR (600 MHz, DMSO) δ 10.61 (s, 1H), 8.89 (d, J=1.3 Hz, 1H), 8.42 (d, J=1.3 Hz, 1H), 7.90 (m, 2H), 7.20 (dd, J=11.6, 8.9 Hz, 1H), 6.86-6.62 (m, 1H), 6.37 (s, 2H), 4.02 (s, 3H), 2.56-2.50 (m, 2H), 2.19-1.96 (m, 2H).

LC-MS (m/z) 430.1 (MH$^+$); t$_R$ =0.48 minutes (Method A)

EXAMPLE 4

(S)-N-(3-(6-amino-2-(difluoromethyl)-3,3-difluoro-2,3,4,5-tetrahydropyridin-2-yl)-4-fluorophenyl)-2-methyloxazole-4-carboxamide (Compound 4)

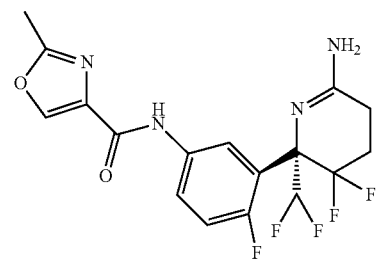

Prepared as in example 1 from (S)-6-(5-amino-2-fluorophenyl)-6-(difluoromethyl)-5,5-difluoropiperidine-2-thione and 2-methyloxazole-4-carboxylic acid.

$^1$H NMR (600 MHz, DMSO) δ 10.25 (s, 1H), 8.64 (s, 1H), 7.82 (m, 2H), 7.16 (dd, J=11.6, 8.7 Hz, 1H), 6.73 (t, J=55.2 Hz, 1H), 6.36 (s, 2H), 3.01 (s, 1H), 2.59-2.41 (m, 5H), 2.19-1.96 (m, 2H).

LC-MS (m/z) 403 (MH$^+$); t$_R$=0.42 minutes (Method A)

EXAMPLE 5

(S)-N-(3-(6-amino-2-(difluoromethyl)-3,3-difluoro-2,3,4,5-tetrahydropyridin-2-yl)-4-fluorophenyl)-5-methoxypicolinamide (Compound 5)

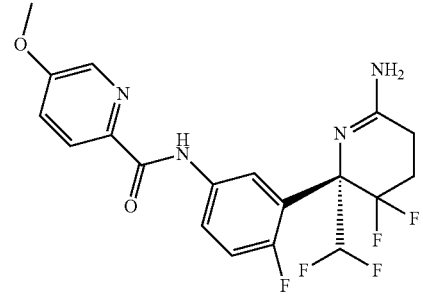 [SMILES: COc1ccc(C(=O)Nc2ccc(F)c([C@@]3(C(F)F)N=C(N)CCC3(F)F)c2)nc1]

Prepared as in example 1 from (S)-6-(5-amino-2-fluorophenyl)-6-(difluoromethyl)-5,5-difluoropiperidine-2-thione and 5-methoxypicolinic acid.

$^1$H NMR (600 MHz, DMSO) δ 10.55 (s, 1H), 8.40 (d, J=2.9 Hz, 1H), 8.13 (d, J=8.7 Hz, 1H), 7.94-7.90 (m, 1H), 7.84 (dd, J=6.7, 2.7 Hz, 1H), 7.62 (dd, J=8.7, 2.9 Hz, 1H), 7.18 (dd, J=11.6, 8.8 Hz, 1H), 6.85-6.61 (m, 1H), 6.36 (s, 2H), 3.93 (s, 3H), 2.55-2.47 (m, 2H), 2.17-2.00 (m, 2H).

LC-MS (m/z) 429.1 (MH$^+$); t$_R$=0.5 minutes (Method A)

EXAMPLE 6

(S)-N-(3-(6-amino-2-(difluoromethyl)-3,3-difluoro-2,3,4,5-tetrahydropyridin-2-yl)-4-fluorophenyl)-5-(difluoromethyl)pyrazine-2-carboxamide (Compound 6)

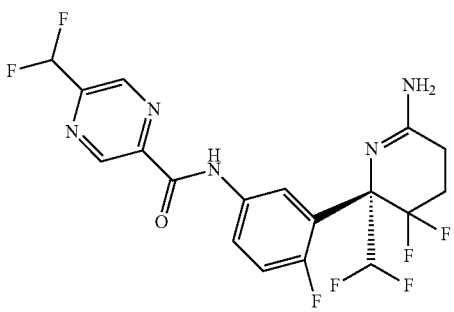 [SMILES: NC1=N[C@@](c2cc(NC(=O)c3cnc(C(F)F)cn3)ccc2F)(C(F)F)C(F)(F)CC1]

Prepared as in example 1 from (S)-6-(5-amino-2-fluorophenyl)-6-(difluoromethyl)-5,5-difluoropiperidine-2-thione and 5-difluoromethyl)pyrazine-2-carboxylic acid.

$^1$H NMR (600 MHz, DMSO) δ 11.02 (s, 1H), 9.40 (d, J=1.3 Hz, 1H), 9.10 (s, 1H), 7.96-7.91 (m, 2H), 7.38-7.17 (m, 2H), 6.75 (t, J=55.1 Hz, 1H), 6.38 (s, 2H), 2.56-2.50 (m, 2H), 2.20-1.98 (m, 2H).

LC-MS (m/z) 450.1 (MH$^+$); $t_R$=0.48 minutes (Method A)

EXAMPLE 7

(S)-N-(3-(6-amino-2-(difluoromethyl)-3,3-difluoro-2,3,4,5-tetrahydropyridin-2-yl)-4-fluorophenyl)-5-cyanopicolinamide (Compound 7)

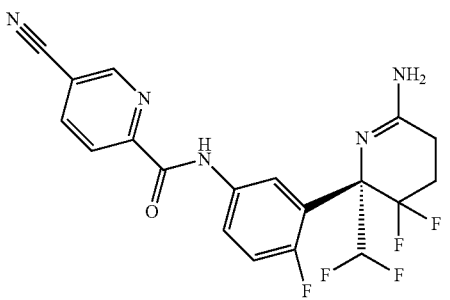 [SMILES: N#Cc1ccc(C(=O)Nc2ccc(F)c([C@@]3(C(F)F)N=C(N)CCC3(F)F)c2)nc1]

Prepared as in example 1 from (S)-6-(5-amino-2-fluorophenyl)-6-(difluoromethyl)-5,5-difluoropiperidine-2-thione and 5-cyanopicolinic acid.

$^1$H NMR (600 MHz, DMSO) δ 10.94 (s, 1H), 9.21 (d, J=1.3 Hz, 1H), 8.59 (dd, J=8.2, 1.9 Hz, 1H), 8.29 (d, J=8.1 Hz, 1H), 7.96-7.88 (m, 2H), 7.22 (dd, J=11.5, 8.8 Hz, 1H), 6.74 (t, J=55.0 Hz, 1H), 6.37 (s, 2H), 2.57-2.48 (m, 2H), 2.07 (m, 2H).

LC-MS (m/z) 424.5 (MH$^+$); $t_R$=0.45 minutes (Method B)

EXAMPLE 8

(S)-N-(3-(6-amino-2-(difluoromethyl)-3,3-difluoro-2,3,4,5-tetrahydropyridin-2-yl)-4-fluoro-phenyl)-4-methylthiazole-2-carboxamide (Compound 8)

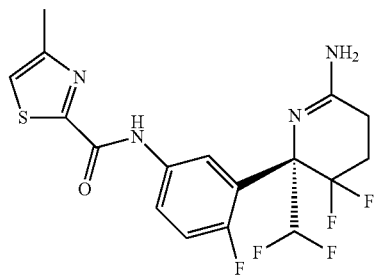 [SMILES: Cc1csc(C(=O)Nc2ccc(F)c([C@@]3(C(F)F)N=C(N)CCC3(F)F)c2)n1]

Prepared as in example 1 from (S)-6-(5-amino-2-fluorophenyl)-6-(difluoromethyl)-5,5-difluoropiperidine-2-thione and 4-methylthiazole-2-carboxylic acid.

$^1$H NMR (600 MHz, DMSO) δ 10.84 (s, 1H), 7.90 (dd, J=6.7, 2.5 Hz, 1H), 7.88-7.83 (m, 1H), 7.70 (s, 1H), 7.19 (dd, J=11.5, 8.9 Hz, 1H), 6.74 (t, J=55.1 Hz, 1H), 6.38 (s, 2H), 2.59-2.46 (m, 5H), 2.18-1.95 (m, 2H).

LC-MS (m/z) 419.4 (MH$^+$); $t_R$=0.47 minutes (Method B)

EXAMPLE 9

(S)-N-(3-(6-amino-2-(difluoromethyl)-3,3-difluoro-2,3,4,5-tetrahydropyridin-2-yl)-4-fluorophenyl)-5-methoxypyrimidine-2-carboxamide (Compound 9)

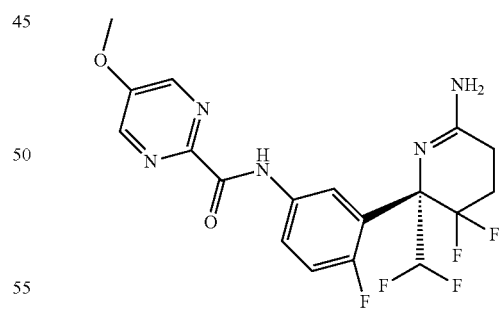

Prepared as in example 1 from (S)-6-(5-amino-2-fluorophenyl)-6-(difluoromethyl)-5,5-difluoropiperidine-2-thione and 5-methoxypyrimidine-2-carboxylic acid.

$^1$H NMR (600 MHz, DMSO) δ 10.73 (s, 1H), 8.73 (s, 2H), 7.95-7.91 (m, 1H), 7.82 (dd, J=6.7, 2.5 Hz, 1H), 7.22-7.18 (m, 1H), 6.74 (t, J=55.2 Hz, 1H), 6.37 (s, 2H), 4.03 (s, 3H), 2.58-2.50 (m, 2H), 2.18-1.99 (m, 2H).

LC-MS (m/z) 430.5 (MH$^+$); $t_R$=0.39 minutes (Method B)

EXAMPLE 10

(S)-N-(3-(6-amino-2-(difluoromethyl)-3,3-difluoro-2,3,4,5-tetrahydropyridin-2-yl)-4-fluorophenyl)-5-methoxy-3-methylpyrazine-2-carboxamide (Compound 10)

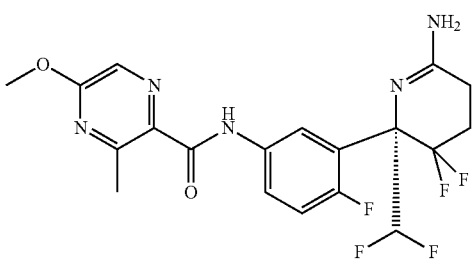 [SMILES: COc1cnc(C(=O)Nc2ccc(F)c([C@@]3(C(F)F)N=C(N)CCC3(F)F)c2)c(C)n1]

Prepared as in example 1 from (S)-6-(5-amino-2-fluorophenyl)-6-(difluoromethyl)-5,5-difluoropiperidine-2-thione and 5-methoxy-3-methylpyrazine-2-carboxylic acid.

$^1$H NMR (600 MHz, DMSO) δ 10.52 (s, 1H), 8.24 (d, J=0.6 Hz, 1H), 7.91 (ddd, J=8.8, 4.1, 2.8 Hz, 1H), 7.74 (dd, J=6.8, 2.7 Hz, 1H), 7.18 (dd, J=11.7, 8.8 Hz, 1H), 6.85-6.62 (m, 1H), 6.38 (s, 2H), 3.99 (s, 3H), 2.76 (d, J=0.5 Hz, 3H), 2.55-2.49 (m, 2H), 2.18-1.99 (m, 2H).

LC-MS (m/z) 444.5 (MH$^+$); $t_R$=0.52 minutes (Method B)

EXAMPLE 11

(S)-N-(3-(6-amino-2-(difluoromethyl)-3,3-difluoro-2,3,4,5-tetrahydropyridin-2-yl)-4-fluorophenyl)-5-cyano-3-methylpicolinamide (Compound 11)

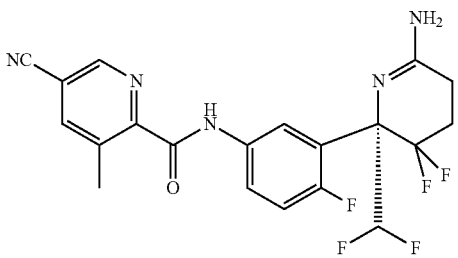 [SMILES: Cc1cc(C#N)cnc1C(=O)Nc1ccc(F)c([C@@]2(C(F)F)N=C(N)CCC2(F)F)c1]

Prepared as in example 1 from (S)-6-(5-amino-2-fluorophenyl)-6-(difluoromethyl)-5,5-difluoropiperidine-2-thione and 5-cyano-3-methylpicolinic acid.

$^1$H NMR (600 MHz, DMSO) δ 10.80 (s, J=27.6 Hz, 1H), 8.99 (d, J=1.2 Hz, 1H), 8.40 (s, 1H), 7.99-7.87 (m, 1H), 7.82-7.69 (m, 1H), 7.36-7.13 (m, 1H), 6.73 (t, J=55.0 Hz, 1H), 6.36 (s, 2H), 2.56-2.47 (m, 2H), 2.21-1.97 (m, 2H).

LC-MS (m/z) 438.1 (MH$^+$); $t_R$=0.49 minutes (Method B)

EXAMPLE 12

(S)-N-(3-(6-amino-2-(difluoromethyl)-3,3-difluoro-2,3,4,5-tetrahydropyridin-2-yl)-4-fluorophenyl)-5-bromopicolinamide (Compound 12)

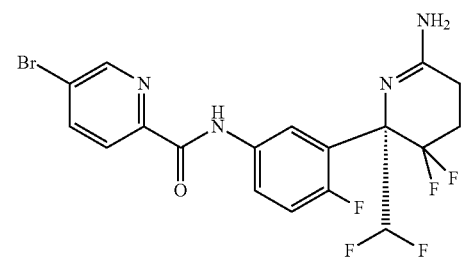 [SMILES: NC1=N[C@@](c2cc(NC(=O)c3ccc(Br)cn3)ccc2F)(C(F)F)C(F)(F)CC1]

Prepared as in example 1 from (S)-6-(5-amino-2-fluorophenyl)-6-(difluoromethyl)-5,5-difluoropiperidine-2-thione and 5-bromopicolinic acid.

$^1$H NMR (600 MHz, DMSO) δ 10.78 (s, 1H), 8.87 (dd, J=2.3, 0.7 Hz, 1H), 8.33 (dd, J=8.4, 2.3 Hz, 1H), 8.09 (dd, J=8.4, 0.6 Hz, 1H), 7.94 (ddd, J=8.8, 4.1, 2.8 Hz, 1H), 7.89 (dd, J=6.8, 2.7 Hz, 1H), 7.21 (dd, J=11.6, 8.8 Hz, 1H), 6.88-6.62 (m, 1H), 6.39 (s, 2H), 2.60-2.49 (m, 2H), 2.19-1.96 (m, 2H).

LC-MS (m/z) 479.1 (MH$^+$); $t_R$=0.53 minutes (Method B)

EXAMPLE 13

(S)-N-(3-(6-amino-2-(difluoromethyl)-3,3-difluoro-2,3,4,5-tetrahydropyridin-2-yl)-4-fluorophenyl)-5-(methoxy-d3)picolinamide (Compound 13)

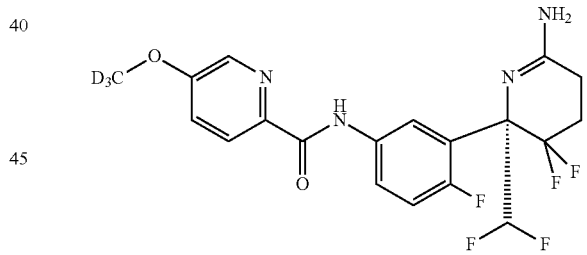

(S)-6-(5-amino-2-fluorophenyl)-6-(difluoromethyl)-5,5-difluoropiperidine-2-thione (25 mg, 0.081 mmol) in was dissolved in dichloromethane (1 mL) under an atmosphere of argon. Trimethylaluminum (52 µl, 0.105 mmol, 2 molar, toluene) was added slowly, then methyl-(methoxy-d3)picolinate (18 mg, 0.11 mmol) in 0.5 mL dichloromethane was added. The reaction mixture was stirred at room temperature for 2 hours. The reaction mixture was poured into cooled 4N HCl (aq). The mixture was extracted with ethyl acetate. The organic phase was washed with brine, dried over magnesium sulphate and concentrated in vacuo. 7M ammonia in methanol (4 mL) was added and the reaction mixture was stirred in a sealed vial at 50° C. overnight. The reaction mixture was concentrated in vacuo and was purified by flash chromatography on silica gel (heptane/ethyl acetate) followd by purification by preperative HPLC to obtain the title compound as the trifluroacetic acid salt.

$^1$H NMR (600 MHz, DMSO) δ 11.13 (s, 1H), 10.75 (s, 1H), 9.98 (s, 1H), 9.10 (s, 1H), 8.40 (dd, J=2.9, 0.5 Hz, 1H), 8.21 (ddd, J=8.9, 4.1, 2.6 Hz, 1H), 8.15 (dd, J=8.7, 0.5 Hz, 1H), 8.09 (dd, J=6.8, 2.6 Hz, 1H), 7.64 (dd, J=8.7, 2.9 Hz, 1H), 7.40 (dd, J=11.9, 9.0 Hz, 1H), 7.20 (t, J=53.0 Hz, 1H), 3.17-3.01 (m, 2H), 2.48-2.38 (m, 2H).

LC-MS (m/z) 432 (MH$^+$); $t_R$=0.49 minutes (Method A)

EXAMPLE 14

(S)-N-(3-(6-amino-2-(difluoromethyl)-3,3-difluoro-2,3,4,5-tetrahydropyridin-2-yl)-4-fluorophenyl)-5-(methoxy-d3)pyrazine-2-carboxamide (Compound 14)

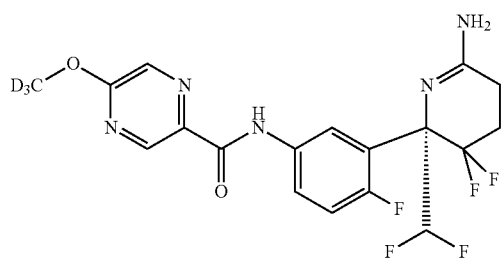 [SMILES: [2H]C([2H])([2H])Oc1cnc(C(=O)Nc2ccc(F)c([C@@]3(C(F)F)N=C(N)CCC3(F)F)c2)cn1]

Prepared as in example 13 from (S)-6-(5-amino-2-fluorophenyl)-6-(difluoromethyl)-5,5-difluoropiperidine-2-thione and methyl 5-(methoxy-d$_3$)picolinate.

$^1$H NMR (600 MHz, DMSO) δ 10.61 (s, 1H), 8.89 (d, J=1.2Hz, 1H), 8.42 (d, J=1.2Hz, 1H), 7.91-7.86 (m, 2H), 7.19 (dd, J=11.5, 8.9 Hz, 1H), 6.84-6.61 (m, 1H), 6.36 (s, 2H), 2.53-2.49 (m, 2H), 2.16-1.96 (m, 2H).

LC-MS (m/z) 433.1 (MH$^+$); $t_R$ =0.49 minutes (Method A)

Stereochemistry

Crystals were obtained by recrystallization of (S)-5-bromo-N-(3-(2-(difluoromethyl)-3,3-difluoro-6-thioxopiperidin-2-yl)-4-fluorophenyl)picolinamide from a mixture of heptane and ethyl acetate. The structure of (S)-5-bromo-N-(3-(2-(difluoromethyl)-3,3-difluoro-6-thioxopiperidin-2-yl)-4-fluorophenyl)picolinamide (FIG. 1) was elucidated by X-ray crystallography of said crystals. The structure shows the absolute and relative configuration of (S)-5-bromo-N-(3-(2-(difluoromethyl)-3,3-difluoro-6-thioxopiperidin-2-yl)-4-fluorophenyl)picolinamide. (S)-5-bromo-N-(3-(2-(difluoromethyl)-3,3-difluoro-6-thioxopiperidin-2-yl)-4-fluorophenyl)picolinamide was prepared as described in example 1 starting from (S)-6-(5-amino-2-fluorophenyl)-6-(difluoromethyl)-5,5-difluoropiperidine-2-thione and 5-bromopicolinic acid.

The absolute configurations of the exemplified compounds of the present invention can thus be rationalized. (S)-5-bromo-N-(3-(2-(difluoromethyl)-3,3-difluoro-6-thioxopiperidin-2-yl)-4-fluorophenyl)picolinamide was prepared from (S)-6-(5-amino-2-fluorophenyl)-6-(difluoromethyl)-5,5-difluoropiperidine-2-thione which is staring material for all exemplified compounds of the present invention.

Pharmacological Testing

BACE1 Binding Assay

The binding assay was performed as SPA-based assay using a biotinylated form of human BACE1 recombinantly expressed and subsequently purified from Freestyle HEK293 cells. The binding assay was run in a 50 mM sodium acetate buffer, pH 4.5 containing 50 mM NaCl and 0.03% Tween-20 in white clear bottom 384 plates (Corning #3653). 10 nM (final concentration) radioligand ([$^3$H]-N-((1S,2R)-1-benzyl-3-cyclopropylamino-2-hydroxy-propyl)-5-(methanesulfonyl-methyl-amino)-N#R)-1-phenyl-ethyl)-isophthalamide) (TRQ11569 purchased from GE Healthcare) was mixed with test compound at a given concentration, 6 nM (final concentration) human BACE1 and 25 µg Streptavidin coated PVT core SPA beads (RPNQ0007, GE Healthcare Life Sciences) in a total volume of 40 µl. Several concentrations of each test compound were tested in the assay for IC$_{50}$ determination. The plates were incubated for one hour at room temperature and counted in a Wallac Trilux counter. Total and non-specific binding were determined using buffer and 1 µM (final concentration) of the high affinity BACE1 reference inhibitor (S)-6-[3-chloro-5-(5-prop-1-ynyl-pyridin-3-yl)-thiophen-2-yl]-2-imino-3,6-dimethyl-tetrahydro-pyrimidin-4-one, respectively. For each test compound, a IC$_{50}$ value (the concentration mediating 50% inhibition of the specific binding of the radioligand) was determined from concentration-response curve and used to calculate the K$_i$ from the equation K$_i$=IC$_{50}$/(1+L/K$_d$), where L and K$_d$ are the final concentration of the radioligand used in the assay and the dissociation constant of the radioligand, respectively. The K$_d$ of the radioligand was determined from saturation binding experiments.

TABLE 1 binding affinity of selected compounds

| Compound No | BACE1 Ki (nM) |
|---|---|
| 1 | 18 |
| 2 | 23 |
| 3 | 8.5 |
| 4 | 20 |
| 5 | 6.7 |
| 6 | 20 |
| 7 | 7.4 |
| 8 | 71 |
| 9 | 6.9 |
| 10 | 16 |
| 11 | 7.8 |
| 12 | 6.1 |
| 13 | 14 |
| 14 | 18 |

BACE1 Efficacy Assay

The efficacy assay was performed as a FRET-based assay using a commercially available BACE1 kit (Life Technologies, P2985). 2 µl test compound at 10 µM (final concentration) and 15 µl BACE1 enzyme from the kit (final concentration 3 nM) were preincubated for 15 minutes at room temperature before addition of 15 µl of substrate from the kit (250 nM final concentration) and incubated for additional 90 minutes at room temperature. The assay plate was subsequently read in a Pherastar (Ex540/Em590). The enzyme activity observed in presence of test compound were normalized to the enzyme activity observed in presence of buffer and 10 µM (final concentration) of the high affinity BACE1 reference inhibitor (S)-6-[3-Chloro-5-(5-prop-1-ynyl-pyridin-3-yl)-thiophen-2-yl] -2-imino-3,6-dimethyl-tetra-hydropyrimidin-4-one, respectively. The efficacy of the test compounds was evaluated at 10 µM (final concentration) and defined as the percent inhibition of the enzyme activity using the equation %inhibition=100% -normalized enzyme activity in percent.

TABLE 2

BACE1 activity of selected compounds

| CompoundNo | BACE1 inhibition at 10 µM (%) |
|---|---|
| 1 | 106 |
| 2 | 100 |
| 3 | 103 |
| 4 | 104 |
| 5 | 101 |
| 6 | 103 |
| 8 | 102 |
| 9 | 103 |
| 10 | 106 |
| 13 | 103 |
| 14 | 108 |

Assessment of Aβ Levels in Rat Brain and Plasma Following BACE1 Inhibition. Animals.

All rat care and experimental procedures were approved by Lundbeck Veterinary Staff, according to Danish legislature. The rats were maintained in a barrier facility with a 12/12-h light/dark cycle and ad libitum food and water access.

Treatment of Naïve Rats.

Young adult Male Sprague Dawley rats of approximately 250 g weight were purchased from Charles River and received 0-30 mg/kg of vehicle (10% HP betaCD+1M MeSO$_4$, pH 2.5) or test compounds (dissolved in vehicle) only by oral gavage (p.o). The compounds are dosed at a volume of 5 ml/kg. Cohorts of 5-10 animals were established for each treatment condition.

The animals undergoing treatment were closely monitored by veterinary staff for any signs of toxicity. Monitoring parameters included body weight, physical appearance, changes in coat appearance, occurrence of unprovoked behavior, and blunted or exaggerated responses to external stimuli.

Tissue Collection.

At T=180 minutes after initial dosing the animals were stunned and decapitated with a guillotine. Trunk-blood was sampled in EDTA coated tubes after decapitation of the animal. The blood was centrifuged at 2200G at 4° C. for 15 minutes and the plasma was collected and frozen at −80° C. The blood was aliquoted for Aβ ELISA and DMPK analysis Immediately following sacrifice, the brain was extracted and split into 2 halves. The right hemibrains were snap frozen on dry ice and stored at −80° C. The left half was dissected; with the front forebrain taken for Aβ ELISA and the remainder used for DMPK analysis. These samples were also snap frozen on dry ice and stored at −80° C. until use for analysis.

Tissue Processing.

The cortex samples were thawed slightly on wet ice before they were homogenized with a small volume dispersing instrument (T10 basic ULTRA-TURRAX®) which was set at speed 5 for approximately 5-7 sec. The tissue was processed in a 10 times volume of the weight, for example 100 mg of tissue was homogenized in 1000 µL of Homogenization buffer. Homogenization buffer: 50 ml Milli Q water+50 nM NaCl+0.2% Diethylamin (DEA)+1 tablet of Complete Protease inhibitor cocktail+1 nM 4-(2-aminoethyl) benzenesulfonyl fluoride hydrochloride irreversible serine protease inhibitor (AEBSF).

After homogenization 450 µL aliquots of the samples are collected into a 1.5 ml Eppendorf tube and placed on wet ice, 0.5% NP-40 (50 ul ) was added to all samples and then they were incubated on ice for 30 min. After which all samples were sonicated using an Ultrasonic homogenizer with 20 kHz homogeneous sound (SONOPLUS HD2070, Bandelin Electronic) 10 pulse set at 12-13% power to extract all the Aβ species. The samples were then centrifuged (Ole Dich 157 MPRF Micro centrifuge) at 20000 G for 20 minutes at 4° C. After centrifugation 285 µL of the supernatant was pipetted into 600 µL microtubes tubes and neutralized with 15 µL of 1M Tris-HCL buffer.

ELISA Protocol.

WAKO 294-62501 Human/Rat Abeta amyloid (40) kit was used for all ELISA analyses. 30 µL plasma samples or 30 µL of the cortex supernatants generated as described above were placed in 600 µL microtubes tubes on wet ice. To this 30 µL of 8M Urea (AppliChem A1049, 9025) are added to generate a 2-fold dilution. Both plasma and cortex supernatants are incubated on ice for 30 min. Standard rows were prepared from the standard peptide stock provided in the kit and standard diluent containing 1.6M Urea (200 µL 8M Urea+800 µL of standard diluent) and 0.8M Urea (400 µL 8M Urea+3600 µL Standard diluent). A serial 2-fold dilution of Aβ40 from 100 pmol/ml to 0 pmol/L was prepared for the assay.

After incubation with urea, all samples were further diluted by addition of 5 times standard diluent from the Kit. This was done by adding 240 µL Standard Diluent to 60 µL sample/urea mixture, which was then mixed well. 100 µL of each diluted sample was pipetted into designated wells of the ELISA plate in duplicates. The plate was then covered and incubated overnight at 4° C. The following day, the ELISA kit was brought to room temperature before use. The incubated plate was washed 5 times with the 20× washing solution diluted in Milli Q water. 100 µL HRP-conjugate was applied to each well, and the plate was covered and incubates at 4° C. for 1 hr. The wash was repeated again for 5 times. 100 µL 3,3',5,5'-Tetramethylbenzidine (TMB) solution was applied to each well and the plate was covered and incubated in the dark at room temperature for 30 minutes. 100 µL STOP-solution was next applied to each well, and the plate was read at 450 nm wavelength in a spectrophotometer (Labsystems Multiscan Ascent) within 30 min of adding the STOP-solution to the wells.

Concentration of Aβ in the samples was determined based on a standard curve generated from standards containing known concentrations of synthetic Aβ40.Those skilled in the art will appreciate that diethylamine (DEA) and urea extractions will release soluble Aβ, and insoluble Aβ respectively. Since the ELISA kit is validated and widely used, it is accepted that as long as the treatment conditions and assay conditions are the same for each compound tested, then the assay should yield consistent robust data for the compounds tested and produce minimal discrepancies.

Data Analysis

To determine the concentration of Aβ40 in the samples, the interpolated values of the samples loaded on plates are multiplied by 20 to account for the dilutions made when the volumes of DEA, urea and neutralization solution were added up. Values are calculated as percentage change in Aβ40 compared to vehicle treated animals.

Bioanalysis of Brain and Plasma Samples

TC was determined in plasma and brain homogenate using UltraPerformance LC® (UPLC®) chromatography followed by tandem-MS (MS/MS) detection.

Apparatus:

Tecan Genesis RSP 200; Biomek NXP, Beckman Coulter; Sigma 4K15 centrifuge; Acquity UPLC, Waters; Sciex API4000 TQ, Applied Biosystems; MS software: Analyst version 1.4.1

Chemicals

Acetonitrile, HPLC-grade, Fluka, No. 34967N; Methanol, HPLC-grade, Sigma-Aldrich, Lot 9003S; Formic acid, HPLC-grade, Riedel-de Haën, Lot 51660; Purified water, Millipore Synergy UV Sample Preparation Brain homogenate was prepared by homogenizing the brain 1:4 (v/v) with water:2-propanol:DMSO (50:30:20 v/v/v) followed by centrifugation and collection of the supernatant. Calibration standards and QC samples were prepared using a Hamilton robot. 150 µL of ISTD in acetonitrile (1 ng/mL ISTD) was added to 25 µL of calibration standards, QC samples and test samples (plasma and brain homogenate) using a Biomek robot. After centrifugation (6200 g, 4° C., 20 min) 100 µL supernatant from each sample was transferred to a new plate and mixed with 100 µL water with 0.1% formic acid using a Biomek robot (method file InVivo transfer). After a quick centrifugation (6200 g, 4° C., 5 min) the samples were placed in the auto-sampler.

UPLC-MS/MS Analysis

MS/MS detection was done with an Applied Biosystems Sciex API 4000 instrument in positive-ion electrospray ionisation mode. TC and ISTD were detected at a parent>daughter mass to charge ratio (m/z). Nitrogen was used for the nebulizer and collision gases. The peak area correlated linearly with the plasma and brain concentration of the analytes in the range of 1.00-1000 ng/mL plasma and 5.00-5000 ng/g brain (corrected for dilution). If the plasma/brain sample drug concentration was above 1000 ng/mL or 5000 ng/g, the sample was diluted appropriately in blank plasma/blank brain homogenate before analysis.

Chromatographic System

Analytical columns:

Waters Acquity UPLC HSS C18 SB (pH 2-8) 1.8 µm, 2.1x×30 mm.

Mobile phase A: 0.1% aq. formic acid or 0.1% aq. ammonium hydroxide

Mobile phase B: Acetonitrile with 0.1% aq. formic acid or 0.1% aq. ammonium hydroxide.

Weak wash: Methanol

Strong wash: Acetonitrile/Isopropanol/formic acid (50/50/2 v/v/v)

Flow: 0.6 mL/min

Run time: 3 min.

To waste: 0-0.5 min

Temperature: 40° C.

Gradient:

| Time (min) | % A | % B |
|---|---|---|
| 0 | 98 | 2 |
| 0.01 | 98 | 2 |
| 1.5 | 5 | 95 |
| 2 | 5 | 95 |
| 2.2 | 98 | 2 |
| 3 | 98 | 2 |

Compounds 3 and 5 were admistered at doses of 10 mg/kg p.o. and brain and plasma samples were collected at 3 hours post dose and the following exposures were measured as described above.

TABLE 3

Results for compound 3

| | Dose (mg/kg) | Exp (ng/g) | Brain/Plasma ratio | Aβ40 reduction (%) |
|---|---|---|---|---|
| Brain Rat | 10 | 511 | 0.30 | 24 |
| Plasma Rat | | 1682 | | 39 |
| Brain Rat | 30 | 2284 | 0.32 | 38 |
| Plasma Rat | | 7056 | | 42 |

TABLE 4

Results for compound 5

| | Dose (mg/kg) | Exp (ng/g) | Brain/Plasma ratio | Aβ40 reduction (%) |
|---|---|---|---|---|
| Brain Rat | 10 | 187 | 0.28 | 5 |
| Plasma Rat | | 660 | | 40 |
| Brain Rat | 30 | 959 | 0.29 | 36 |
| Plasma Rat | | 3348 | | 49 |

As shown in tables 3 and 4, compounds of the present invention are able to penetrate the blood brain barrier and show efficacy in the CNS.

MDCK-MDR1 Assay

The permeability of the test compounds was assessed in MDCK-MDR1 cells that were cultured to confluency (4-6 days) in a 96 transwell plate. Test compounds were diluted with the transport buffer (HBSS +1% BSA) to a concentration of 0.5 µM and applied to the apical or basolateral side of the cell monolayer. Permeation of the test compounds from A to B direction or B to A direction was determined in triplicate over a 60-minute incubation time at 37° C. and 5% CO2 with a relative humidity of 95%. Test compounds were quantified by LC-MS/MS analysis based on the peaks area ratios of analyte/IS in both the receiver and donor wells of the transwell plate.

The apparent permeability coefficient Papp (cm/s) was calculated using the equation:

$$Papp = (dCr/dt) \times Vr/(A \times C0)$$

Where dCr/dt is the cumulative concentration of compound in the receiver chamber as a function of time (µM/s); Vr is the solution volume in the receiver chamber (0.05 mL on the apical side; 0.25 mL on the basolateral side); A is the surface area for the transport, i.e. 0.0804 $cm^2$ for the area of the monolayer; C0 is the initial concentration in the donor chamber (µM).

Compounds are classified Pgp substrates when efflux ratio (Papp BA/Papp AB) is ≥2.

TABLE 5

BACE1 activity of selected compounds

| Compound | MDCK-MDR1 efflux ratio |
|---|---|
| 1 | 1.16 |
| 2 | 1.75 |
| 3 | 1.22 |
| 4 | 4.01 |
| 5 | 0.99 |
| 6 | 1.36 |
| 7 | 2.43 |
| 8 | 0.92 |
| 9 | 10.99 |
| 10 | 0.98 |
| 11 | 2.68 |
| 12 | 1.31 |
| 13 | 0.83 |

As shown in tables 5, the majority of the exemplified compounds of the present invention have MDCK-MDR1 efflux ratios below 2 and are thus likely to be able to cross the blood brain barrier (E Kerns, L Di, Drug-like Properties: Concepts, Structure Design and Methods (2008) Elsevier).

The invention claimed is:

1. A compound having the structure:

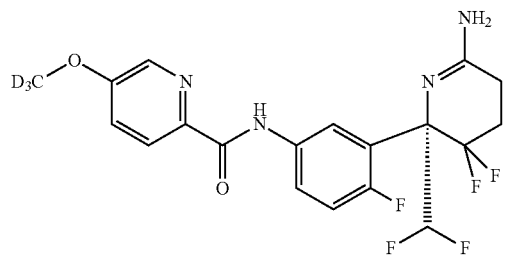 [SMILES: [2H]C([2H])([2H])Oc1ccc(C(=O)Nc2ccc(F)c([C@@]3(C(F)F)N=C(N)CCC3(F)F)c2)nc1]

or a pharmaceutically acceptable salt thereof.

2. A pharmaceutical composition comprising the compound or pharmaceutically acceptable salt thereof according to claim 1 and a pharmaceutically acceptable carrier.

3. A method of treating a neurodegenerative or cognitive disorder or disease, wherein said method comprises administering a therapeutically effective amount of the compound, or pharmaceutically acceptable salt thereof, of claim 1 to a patient in need thereof, wherein said neurodegenerative or cognitive disorder or disease is selected from the group consisting of familial Alzheimer's disease, sporadic Alzheimer's disease, preclinical Alzheimer's disease, prodromal Alzheimer's disease, mild cognitive impairment, Down's syndrome, and cerebral amyloid angiopathy.

* * * * *